(12) United States Patent
Wright et al.

(10) Patent No.: US 9,937,288 B2
(45) Date of Patent: Apr. 10, 2018

(54) DRUG STORAGE AND DISPENSING SYSTEM FOR PRE-FILLED CONTAINERS

(71) Applicant: Becton Dickinson France, Le Pont-de-Claix (FR)

(72) Inventors: Justin Wright, Highland Mills, NY (US); Hervé Monchoix, Montbonnot Saint-Martin (FR); Damien Maréchal, Claix (FR); Amanda Black, Washington, DC (US); Eric Schneider, Catonsville, MD (US); Chet Larrow, Baltimore, MD (US)

(73) Assignee: Becton Dickinson France, Le Pont-de-Claix (FR)

( * ) Notice: Subject to any disclaimer, the term of this patent is extended or adjusted under 35 U.S.C. 154(b) by 17 days.

(21) Appl. No.: 14/996,637

(22) Filed: Jan. 15, 2016

(65) Prior Publication Data
US 2016/0206806 A1    Jul. 21, 2016

Related U.S. Application Data

(60) Provisional application No. 62/104,130, filed on Jan. 16, 2015.

(51) Int. Cl.
*B65D 25/10* (2006.01)
*A61M 5/00* (2006.01)
(Continued)

(52) U.S. Cl.
CPC .......... *A61M 5/002* (2013.01); *A61M 5/008* (2013.01); *A61M 5/3158* (2013.01);
(Continued)

(58) Field of Classification Search
CPC ........ A61M 5/00; A61M 5/002; A61M 5/008; A61M 5/315; A61M 5/3158; A61M 5/32; A61M 5/3204; A61M 2205/14; A61M 2205/50; A61M 2205/60; A61M 2205/6072; B65D 25/10; B65D 25/108
(Continued)

(56) References Cited

U.S. PATENT DOCUMENTS

| | | | |
|---|---|---|---|
| 4,836,373 A | | 6/1989 | Goldman |
| 5,007,535 A | * | 4/1991 | Meseke ................. A61M 5/008 |
| | | | 206/363 |

(Continued)

*Primary Examiner* — Bryon Gehman
(74) *Attorney, Agent, or Firm* — The Webb Law Firm

(57) ABSTRACT

A drug storage and dispensing system that includes a packaging unit and an injection device for pre-filled containers having a needle shield and containing a medication is disclosed. The drug storage and dispensing system of the present disclosure provides for drug administration while minimizing the space occupied by such containers in the cold chain. The packaging unit minimizes the risk of a needle-stick injury, as a healthcare worker does not have to manually remove the needle shield. The injection device provides a novel way of auto-disabling a container, such as a syringe, as a plunger rod is not engaged with the container until the container is actually used. The drug storage and dispensing system provides for a reduction in the number of steps required to perform an injection, and thus a productivity and efficiency gain in mass immunization campaigns.

29 Claims, 37 Drawing Sheets

(51) Int. Cl.
   *A61M 5/315* (2006.01)
   *A61M 5/32* (2006.01)
(52) U.S. Cl.
   CPC ....... *A61M 5/3204* (2013.01); *A61M 2205/14* (2013.01); *A61M 2205/50* (2013.01); *A61M 2205/60* (2013.01); *A61M 2205/6072* (2013.01); *B65D 25/108* (2013.01)
(58) Field of Classification Search
   USPC .................................................. 206/364, 366
   See application file for complete search history.

(56) References Cited

U.S. PATENT DOCUMENTS

| | | | |
|---|---|---|---|
| 5,092,842 A | | 3/1992 | Bechtold et al. |
| 6,270,479 B1 | | 8/2001 | Bergens et al. |
| 7,976,499 B2 | | 7/2011 | Grunhut et al. |
| 8,490,790 B2 | * | 7/2013 | Cocheteux ............ A61M 5/008 206/364 |
| 8,800,800 B2 | * | 8/2014 | Gerner .................. A61M 5/008 220/507 |
| 2009/0270804 A1 | | 10/2009 | Mesa et al. |
| 2009/0318877 A1 | * | 12/2009 | Korn .................... A61M 5/3213 604/198 |
| 2014/0014654 A1 | | 1/2014 | Gerner et al. |
| 2015/0041349 A1 | * | 2/2015 | Liversidge ............ A61M 5/008 206/364 |
| 2015/0190566 A1 | * | 7/2015 | Okihara ................ A61M 5/002 206/365 |

* cited by examiner

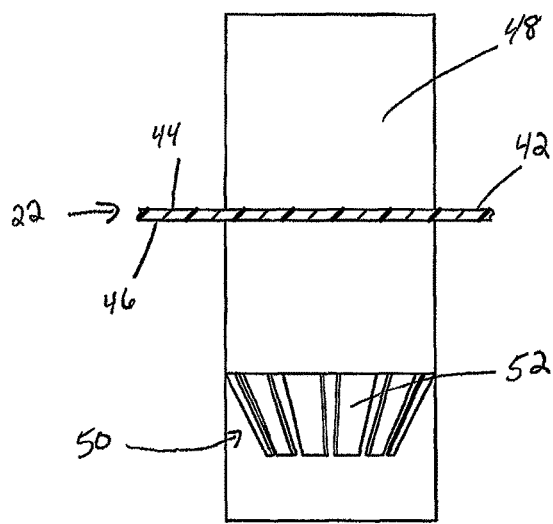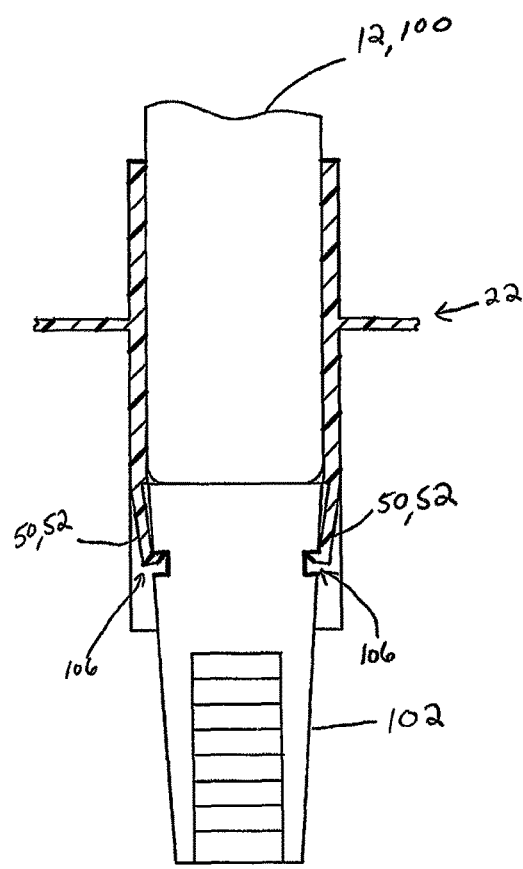
FIG.7A
FIG.7B

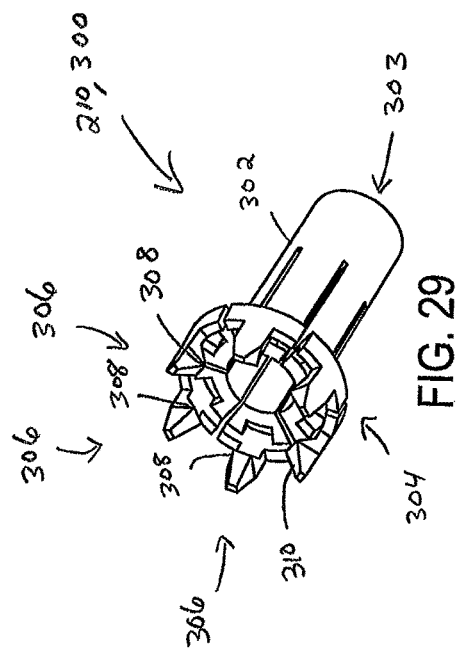
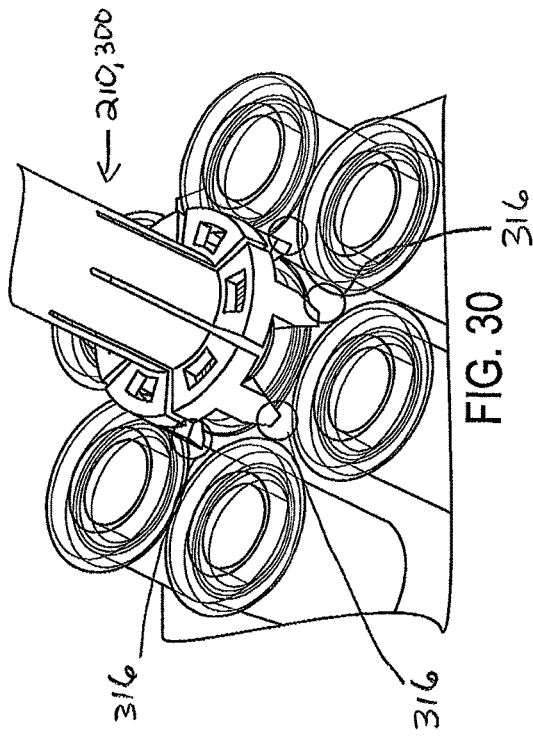
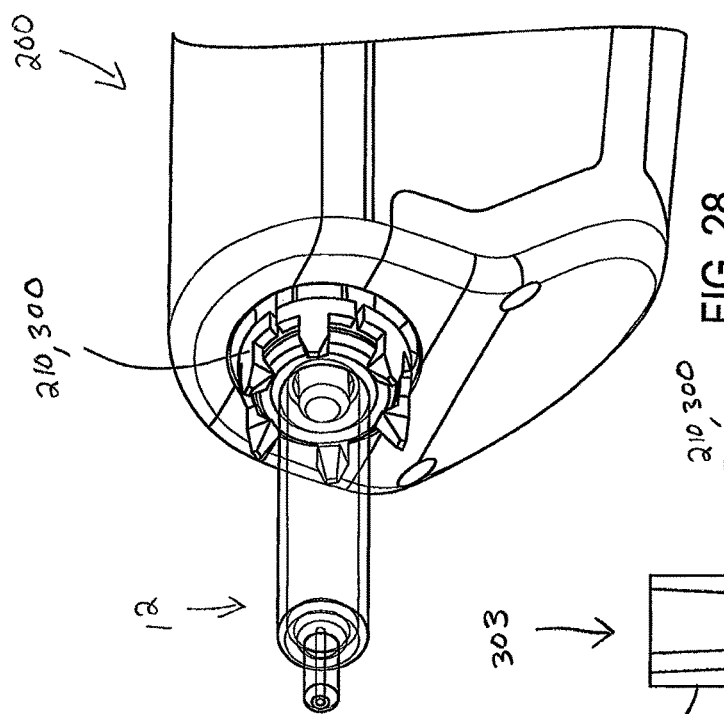
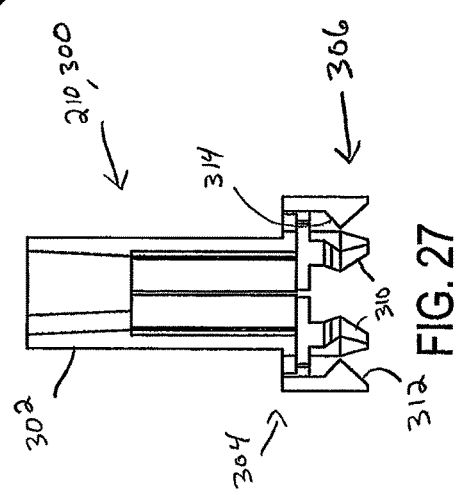

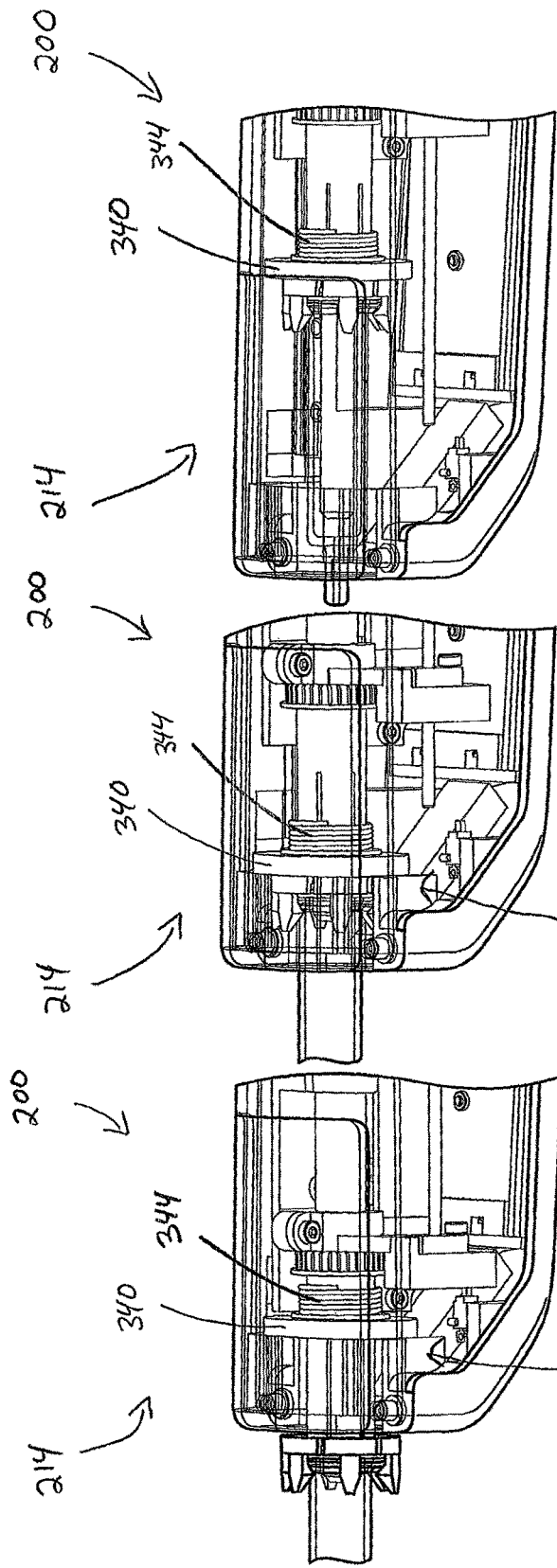

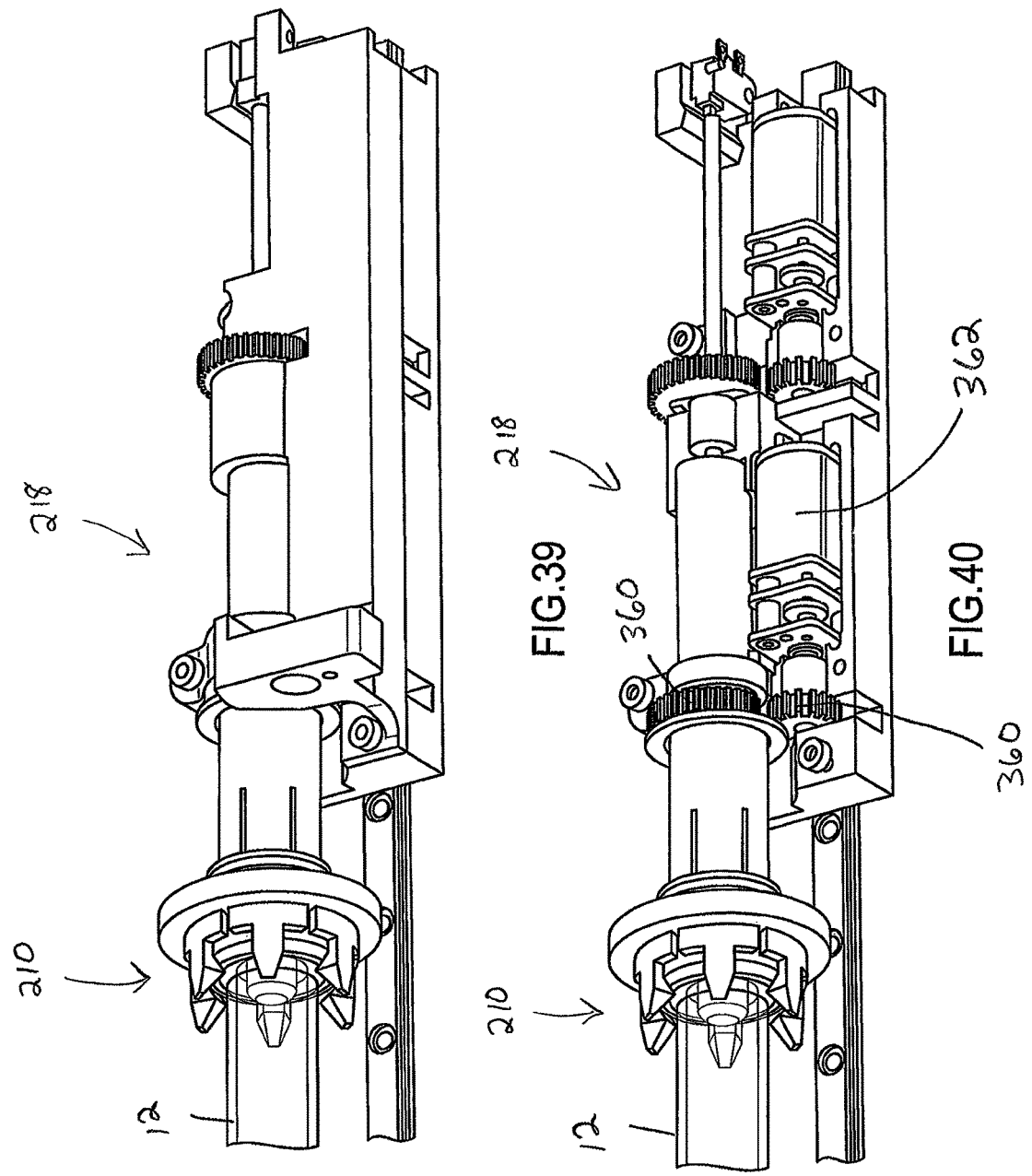

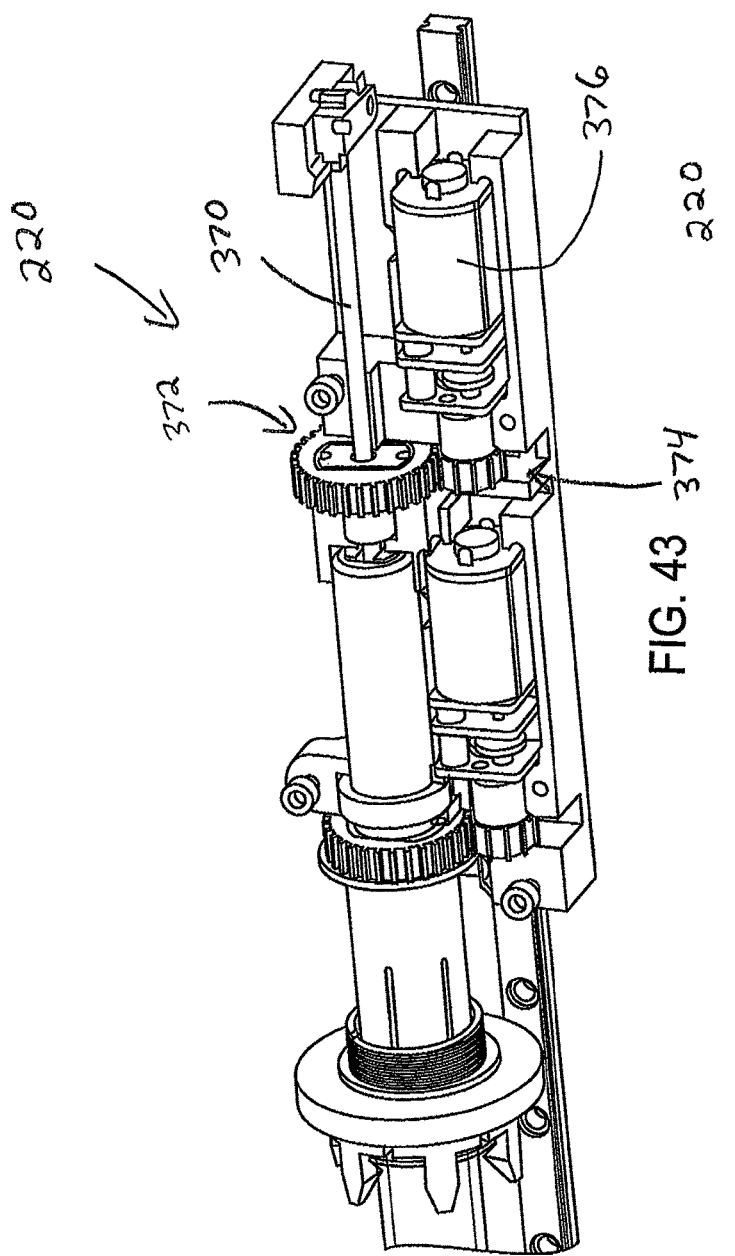
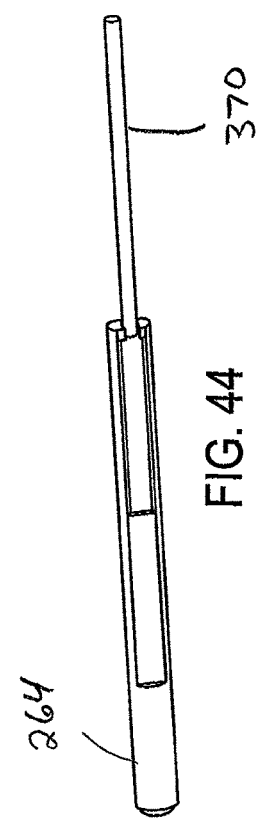
FIG. 43
FIG. 44

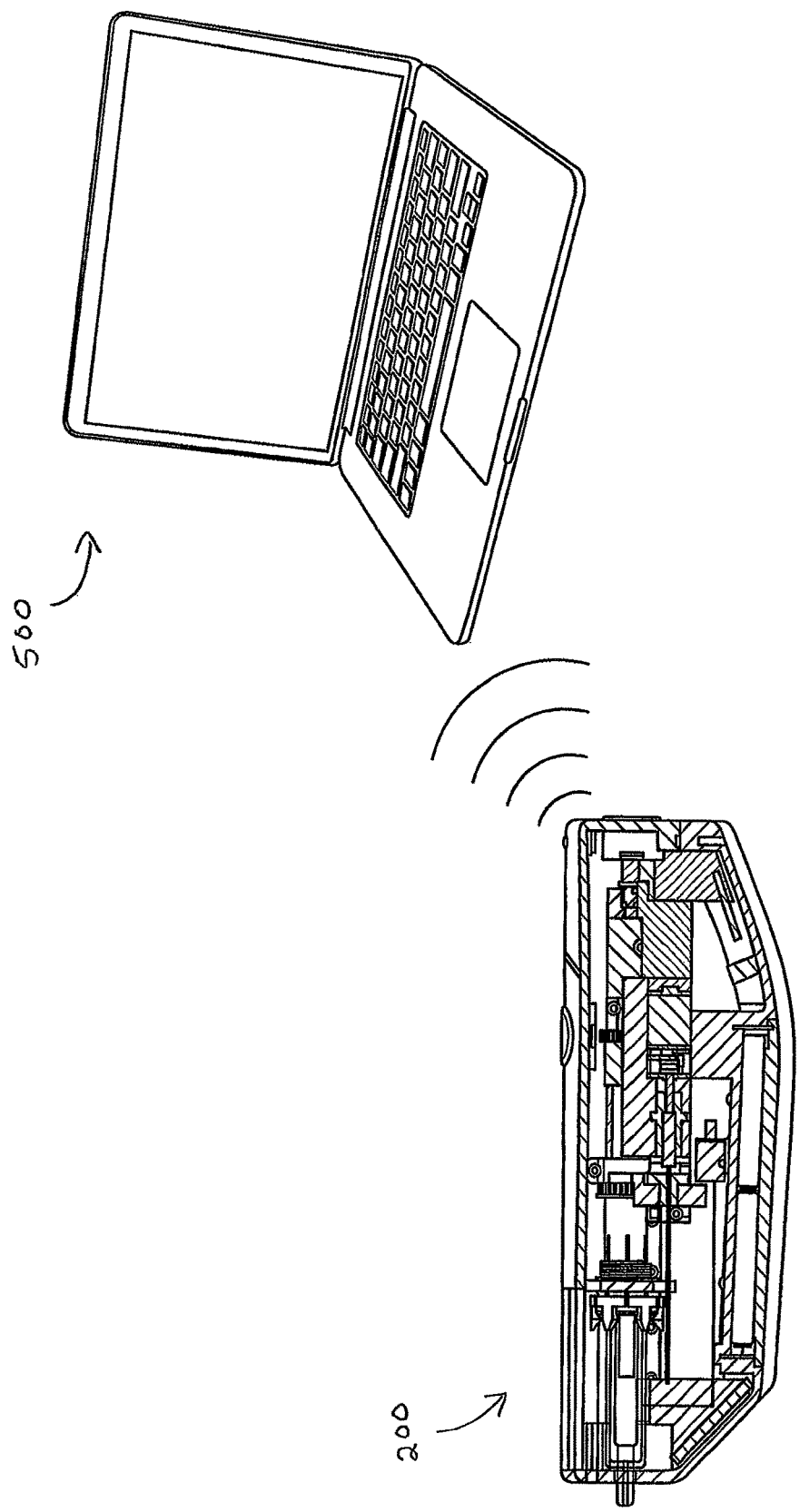

DRUG STORAGE AND DISPENSING SYSTEM FOR PRE-FILLED CONTAINERS

CROSS-REFERENCE TO RELATED APPLICATION

This application claims priority to U.S. Provisional Application Ser. No. 62/104,130, filed Jan. 16, 2015, which is hereby incorporated by reference in its entirety.

BACKGROUND OF THE INVENTION

1. Field of the Disclosure

The present disclosure relates generally to a drug storage and dispensing system. More particularly, the present disclosure relates to a drug storage and dispensing system for pre-filled containers.

2. Description of the Related Art

Conventional syringes are well known in the medical field to be used in connection with a vial of a medication, where the user collects or draws the fluid into the syringe immediately prior to injection and delivery of the fluid to the patient. Commonly, hypodermic syringes may be packaged as "pre-filled" devices, wherein the syringe is pre-filled with a medication prior to being packaged and delivered to the patient. In this manner, the need for the user to fill the device prior to injection is eliminated, thereby saving time and maintaining consistent volumes for delivery.

However, packaging of such pre-filled syringes tends to be bulky and difficult to ship and store. A pre-filled syringe is typically packaged with the opening at the front end of the barrel including a cap thereover and with the plunger rod retracted out of the back end of the syringe barrel, with the fluid pre-filled within the syringe barrel. Such packaging creates an elongated package that can be awkward for shipping and storage.

Pre-filled syringes and pre-filled metered dose syringes are often filled with fluids, such as a medication, at a production facility, packaged, and then shipped to a medical facility. Once at the facility, these syringes are often placed in controlled storage and/or locked cabinets to reduce theft of the syringes themselves and/or of the contents of these syringes. The space within these controlled storage locations is often limited, thus there is a need for a storage format for pre-filled drug containers that minimizes the space occupied by such containers in the cold chain. Cold chain space is one of the inhibitors against conversion to pre-filled containers especially in developing regions.

Further, drug containers need to include information to help medical professionals identify the contents of the drug containers. Errors such as giving an incorrect medication or an incorrect dose can easily be made if the contents of the drug containers cannot be positively identified from the point of time that a medication is transferred to a drug container up to the moment of its administration.

The results of missed and unintended medication include adverse effects to patients and significant costs to the healthcare industry. Potential causes for these errors include unclear drug container contents due to unlabeled or poorly labeled drug containers and poor record keeping of which drugs were administered and the concentration and quantity of the administered drug.

Identifying the content of a drug container based on the appearance of that content is unreliable. Visual identification of the medication is very difficult since several of the medications are identical or nearly identical in appearance.

Furthermore, the protection of used needle tips of a syringe is important to reduce the risk of incurring an accidental needle-stick wound. With concern about infection and transmission of diseases, methods and devices to enclose the used needle have become very important and in great demand.

SUMMARY OF THE INVENTION

The present disclosure provides a drug storage and dispensing system having a packaging unit and an injection device for pre-filled containers having a needle shield and containing a medication. The drug storage and dispensing system of the present disclosure provides for drug administration while minimizing the space occupied by such containers in the cold chain. The packaging unit of the drug storage and dispensing system includes a container holding portion adapted to automatically remove the needle shield of a pre-filled container upon removal of the pre-filled container from the packaging unit. In this manner, the drug storage and dispensing system minimizes the risk of a needle-stick injury, as a healthcare worker does not have to manually remove the needle shield. The injection device of the drug storage and dispensing system provides a novel way of auto-disabling a container, such as a syringe, as a plunger rod is not engaged with the container until the container is actually used. The drug storage and dispensing system provides for a reduction in the number of steps required to perform an injection, and thus a productivity and efficiency gain in mass immunization campaigns. The drug storage and dispensing system provides an automated and secure way to record, store, and transmit the information relative to each injection. The drug storage and dispensing system also provides real-time reconciliation of patient ID, vaccine container ID, vaccination location and time, and the ability to transmit the above information in real-time to a central repository. The drug storage and dispensing system of the present disclosure is especially useful in a pandemic situation where timely and frequent reports of immunization progress over a large population are required.

In accordance with an embodiment of the present invention, a packaging unit for a plurality of pre-filled containers each having a needle shield includes a tub member defining a receiving cavity sized and adapted to receive the plurality of pre-filled containers therein; and a nest member securable within the tub member and having a plurality of container holding portions adapted to receive respective pre-filled containers therein, each of the container holding portions having an engagement member adapted to automatically remove the needle shield of a respective pre-filled container upon removal of the respective pre-filled container from the container holding portion of the packaging unit.

In one configuration, the packaging unit further includes a sealing member removably securable to the tub member. In another configuration, the sealing member is a cover. In yet another configuration, each of the pre-filled containers includes a medication disposed therein. In one configuration, the engagement member includes a plurality of elastically deformable fins.

In accordance with another embodiment of the present invention, a drug storage and dispensing system for a plurality of pre-filled containers each having a needle shield and containing a medication includes a packaging unit including a tub member defining a receiving cavity sized and adapted to receive the plurality of pre-filled containers therein; and a nest member securable within the tub member and having a plurality of container holding portions adapted to receive respective pre-filled containers therein, each of the container holding portions having an engagement member adapted to automatically remove the needle shield of a respective pre-filled container upon removal of the respective pre-filled container from the container holding portion of the packaging unit; and an injection device for automatic injection of the medication from respective pre-filled containers, the injection device having an engagement portion adapted to be removably engageable to each of the respective pre-filled containers, the injection device having a plunger rod movably disposed within the injection device, wherein, with the injection device engaged with a respective pre-filled container, the injection device is adapted to automatically actuate the plunger rod to expel the medication from the respective pre-filled container.

In one configuration, each of the pre-filled containers includes a readable information portion. In another configuration, at least a part of the readable information portion is a barcode. In one configuration, at least a part of the readable information portion is a radiofrequency identification tag. In yet another configuration, the injection device includes a scanner portion adapted to read the readable information portion of respective pre-filled containers. In one configuration, each of the pre-filled containers includes a safety shield adapted to automatically shield a needle tip of a respective pre-filled container after an injection is completed. In another configuration, the engagement portion of the injection device includes a threaded portion.

In accordance with another embodiment of the present invention, a drug storage and dispensing system for a first pre-filled container having a first needle shield and containing a first medication and a second pre-filled container having a second needle shield and containing a second medication includes a packaging unit including a tub member defining a receiving cavity sized and adapted to receive the first pre-filled container and the second pre-filled container therein; and a nest member securable within the tub member and having a first container holding portion adapted to receive the first pre-filled container therein and a second container holding portion adapted to receive the second pre-filled container therein, the first container holding portion having a first engagement member adapted to automatically remove the first needle shield of the first pre-filled container upon removal of the first pre-filled container from the first container holding portion of the packaging unit, the second container holding portion having a second engagement member adapted to automatically remove the second needle shield of the second pre-filled container upon removal of the second pre-filled container from the second container holding portion of the packaging unit; and an injection device for automatic injection of the first medication from the first pre-filled container and the second medication from the second pre-filled container, the injection device having an engagement portion adapted to be removably engageable to the first pre-filled container and the second pre-filled container, the injection device having a plunger rod movably disposed within the injection device, wherein, with the injection device engaged with the first pre-filled container, the injection device is adapted to automatically actuate the plunger rod to expel the first medication from the first pre-filled container, and with the injection device engaged with the second pre-filled container, the injection device is adapted to automatically actuate the plunger rod to expel the second medication from the second pre-filled container.

In one configuration, the first pre-filled container and the second pre-filled container each include a readable information portion. In another configuration, at least a part of the readable information portion is a barcode. In yet another configuration, the injection device includes a scanner portion adapted to read the readable information portion of the first pre-filled container and the second pre-filled container. In one configuration, the first pre-filled container and the second pre-filled container each include a safety shield adapted to automatically shield a respective needle tip of the first pre-filled container and the second pre-filled container after an injection is completed. In another configuration, the engagement portion of the injection device includes a threaded portion. In yet another configuration, at least a part of the readable information portion is a radiofrequency identification tag.

In accordance with another embodiment of the present invention, an injection device for a first pre-filled container having a first medication and a second pre-filled container having a second medication, the injection device comprising an engagement assembly adapted to be removably engageable to the first pre-filled container and the second pre-filled container, the injection device having a plunger rod movably disposed within the injection device, wherein, with the injection device engaged with the first pre-filled container, the injection device is configured to automatically actuate the plunger rod to expel the first medication from the first pre-filled container, and wherein, with the injection device engaged with the second pre-filled container, the injection device is adapted to automatically actuate the plunger rod to expel the second medication from the second pre-filled container.

In one configuration, the engagement assembly comprises a plurality of syringe grip members. In another configuration, the plurality of syringe grip members are elastically deformable. In yet another configuration, the injection device includes a retraction assembly adapted to retract a pre-filled container into the injection device. In one configuration, the retraction assembly is transitionable between a first position in which the plurality of syringe grip members are outside the injection device to engage the pre-filled container and a second position in which the pre-filled container is contained within the injection device. In another configuration, the retraction assembly comprises a rail and a carriage movably attached to the rail. In yet another configuration, with the retraction assembly in the second position with the pre-filled container within the injection device, the injection device further comprises a locking assembly adapted to lock the plurality of syringe grip members to the pre-filled container. In one configuration, the pre-filled container includes a barcode and the injector device further comprises a scan assembly adapted to scan the barcode with the pre-filled container in the second position. In another configuration, the injection device includes a rotation assembly for rotating the pre-filled container with the pre-filled container in the second position. In yet another configuration, the injection device includes an actuator assembly, wherein, with the injection device engaged with the first pre-filled container, the actuator assembly automatically actuates the plunger rod to expel the first medication from the first pre-filled container, and wherein, with the injection device engaged with the second pre-filled container, the actuator assembly automatically actuates the plunger rod to expel the second medication from the second pre-filled container. In one configuration, the injection device includes an ejection assembly adapted to automatically eject a pre-filled container from the injection device.

In accordance with another embodiment of the present invention, a system comprises an injection device for a pre-filled container having a medication and a barcode containing information, the injection device comprising an engagement assembly adapted to be removably engageable to the pre-filled container, a scan assembly adapted to scan the barcode with the pre-filled container contained within the injection device, and a transmitter for transmitting the information; and an electronic database that receives the information transmitted from the injection device, the electronic database adapted to verify the information and transmit a signal to the injection device providing positive feedback for injection using the injection device.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 7A is a side elevation view of a container holding portion of a packaging unit of a drug storage and dispensing system in accordance with an embodiment of the present invention.

FIG. 7B is a cross-sectional view of a container holding portion of a packaging unit of a drug storage and dispensing system engaged with a needle shield of a pre-filled container in accordance with an embodiment of the present invention.

FIG. 27 is a partial cross-sectional view of a portion of an engagement assembly of an injection device in accordance with an embodiment of the present invention.

FIG. 28 is a perspective view of an engagement assembly of an injection device in accordance with an embodiment of the present invention.

FIG. 29 is a perspective view of an engagement assembly of an injection device in accordance with an embodiment of the present invention.

FIG. 30 is a perspective view of an engagement assembly of an injection device engaging a container in a packaging unit in accordance with an embodiment of the present invention.

FIG. 35 is a partial cross-sectional perspective view of an injection device in a first position with a housing hidden to illustrate a locking assembly in accordance with an embodiment of the present invention.

FIG. 36 is a partial cross-sectional perspective view of an injection device in a second position with a housing hidden to illustrate a locking assembly in accordance with an embodiment of the present invention.

FIG. 37 is a partial cross-sectional perspective view of an injection device in a third position with a housing hidden to illustrate a locking assembly in accordance with an embodiment of the present invention.

FIG. 39 is a perspective view of a rotation assembly of an injection device in accordance with an embodiment of the present invention.

FIG. 40 is a perspective view of a rotation assembly of an injection device in accordance with an embodiment of the present invention.

FIG. 43 is a perspective view of an actuator assembly of an injection device in accordance with an embodiment of the present invention.

FIG. 44 is a partial cross-sectional view of a plunger rod of an injection device in accordance with an embodiment of the present invention.

FIG. 48 is a perspective view of a system in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
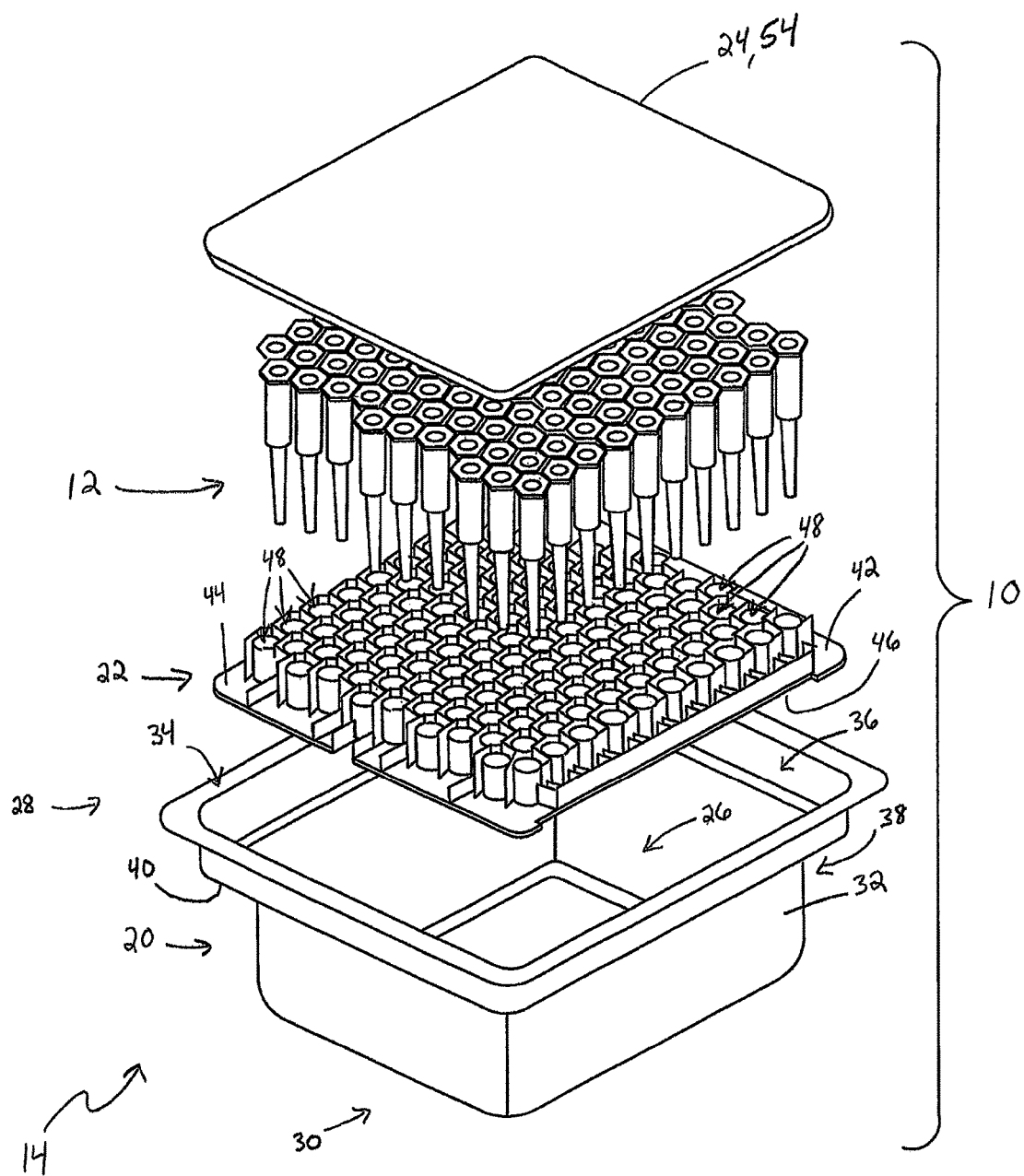
FIG. 1 is an exploded, perspective view of a packaging unit of a drug storage and dispensing system for a plurality of pre-filled containers in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

FIGS. 1-10 illustrate an exemplary embodiment of the present disclosure. Referring to FIGS. 1-10, a drug storage and dispensing system 10 for a plurality of pre-filled containers 12 includes a packaging unit 14 and an injection device 16 as will be described in more detail below. The drug storage and dispensing system 10 of the present disclosure provides for drug storage and administration while minimizing the space occupied by such containers in the cold chain. The packaging unit 14 of the drug storage and dispensing system 10 includes a container holding portion adapted to automatically remove a needle shield of a pre-filled container 12 upon removal of the pre-filled container 12 from the packaging unit 14. In this manner, the drug storage and dispensing system 10 minimizes the risk of a needle-stick injury, as a healthcare worker does not have to manually remove the needle shield. The injection device 16 of the drug storage and dispensing system 10 provides a novel way of auto-disabling a container 12, such as a syringe 100, as a plunger rod is not engaged with the container 12 until the container 12 is actually used. The drug storage and dispensing system 10 provides for a reduction in the number of steps required to perform an injection, and thus a productivity and efficiency gain in mass immunization campaigns.

The drug storage and dispensing system 10 provides an automated and secure way to record, store, and transmit the information relative to each injection. The drug storage and dispensing system 10 also provides real-time reconciliation of patient ID, vaccine container ID, vaccination location and time, and the ability to transmit the above information in real-time to a central repository. The drug storage and dispensing system 10 of the present disclosure is especially useful in a pandemic situation where timely and frequent reports of immunization progress over a large population are required.

The drug storage and dispensing system 10 of the present disclosure is compatible with a plurality of different pre-filled containers. In one embodiment, the drug storage and dispensing system 10 is compatible with syringes 100. For example, the drug storage and dispensing system 10 is compatible with conventionally available syringe from Becton, Dickinson and Company. In some embodiments, the drug storage and dispensing system 10 may be compatible with staked needle syringes and/or luer lock syringes commercially available from Becton, Dickinson and Company. In other embodiments, the drug storage and dispensing system 10 is compatible with other forms of pre-filled containers.

The drug storage and dispensing system 10 of the present disclosure may be used for subcutaneous, intramuscular, or intradermal injection, as well as nasal administration, in the case of Accuspray-equipped syringes, or may be used for other types of injections, for example.

Figure 5A:
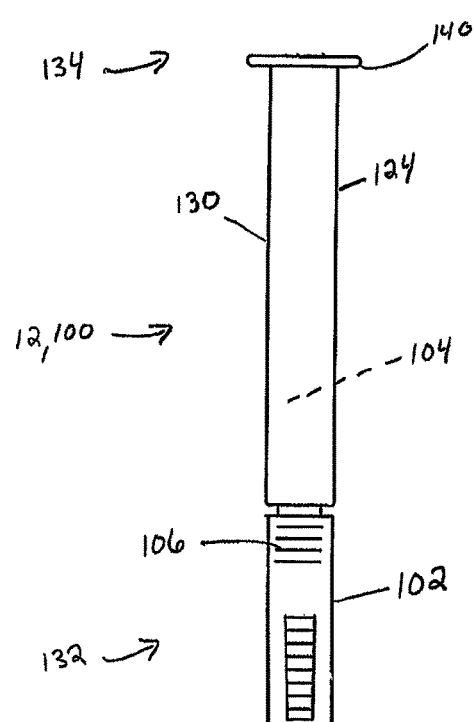
FIG. 5A is a side elevation view of a pre-filled container in accordance with an embodiment of the present invention.

As discussed above, in one embodiment, the pre-filled containers 12 are syringes 100. In one embodiment, the plurality of syringes 100 each include a needle shield 102 and contain a medication 104 disposed therein. Referring to FIGS. 5A and 7B, in one embodiment, the needle shield 102 includes an opening 106 for engagement with a portion of the packaging unit 14 as will be described in more detail below.

Figure 5B:
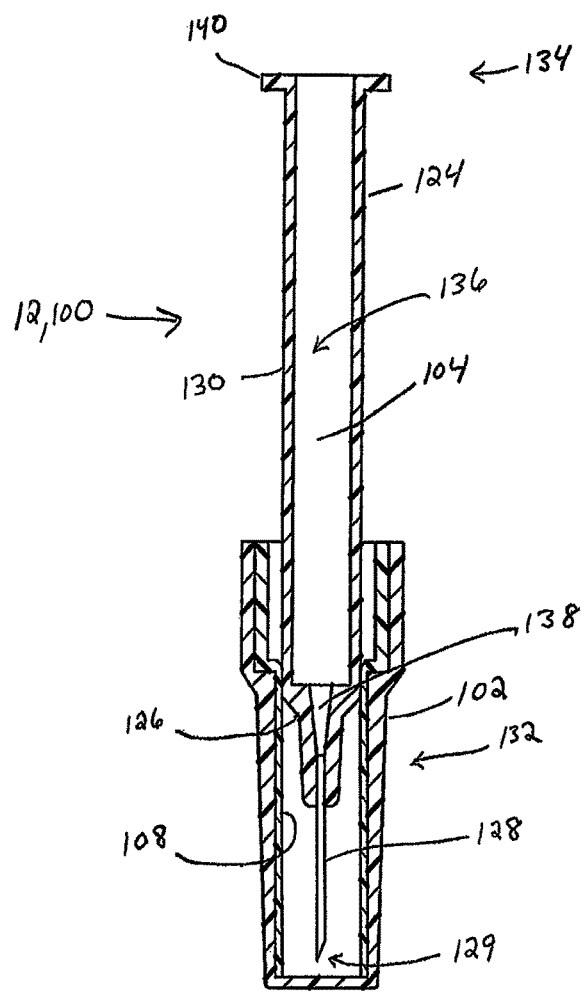
FIG. 5B is a cross-sectional view of a pre-filled container in accordance with another embodiment of the present invention.
Figure 6:
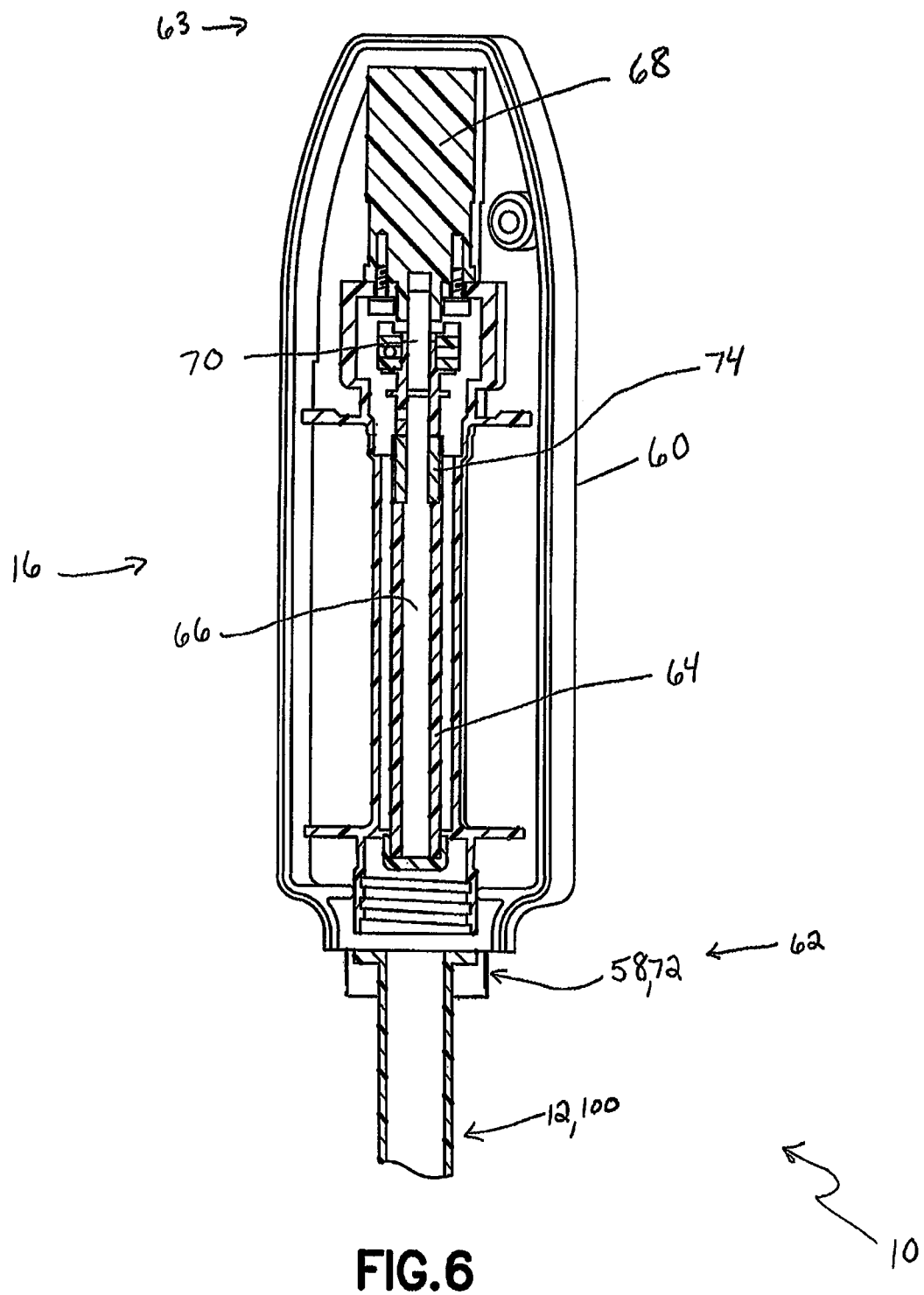
FIG. 6 is a cross-sectional view of an injection device of a drug storage and dispensing system engaged with a pre-filled container in accordance with an embodiment of the present invention.

Referring to FIGS. 5A and 5B, in one embodiment, syringe 100 includes a syringe barrel 124, a needle hub 126, a cannula 128 having a sharp tip 129, needle shield 102 having opening 106, and a safety shield 108. The safety shield 108 is adapted to automatically shield a needle tip of a respective pre-filled container after an injection is completed. Syringe 100 is adapted for dispensing and delivery of a fluid. For example, syringe 100 may be used for injection or infusion of fluid such as a medication into a patient.

Referring to FIGS. 5A and 5B, syringe barrel 124 generally includes a sidewall 130 extending between a first or distal end 132 and a second or proximal end 134. Sidewall 130 defines an elongate aperture or interior chamber 136 of syringe barrel 124. In one embodiment, interior chamber 136 may span the extent of syringe barrel 124 so that syringe barrel 124 is cannulated along its entire length. In one embodiment, syringe barrel 124 may be in the general form of an elongated cylindrical barrel as is known in the art in the general shape of a hypodermic syringe. In alternative embodiments, syringe barrel 124 may be in other forms for containing a fluid for delivery, such as in the general form of an elongated rectangular barrel, for example. Syringe barrel 124 may be formed of glass, or may be injection molded from thermoplastic material such as polypropylene and polyethylene according to techniques known to those of ordinary skill in the art, though it is to be appreciated that syringe barrel 124 may be made from other suitable materials and according to other applicable techniques. In certain configurations, syringe barrel 124 may include an outwardly extending flange 140 about at least a portion of proximal end 134.

Distal end 132 of syringe barrel 124 includes an outlet opening 138 which is in fluid communication with chamber 136. Outlet opening 138 may be sized and adapted for engagement with a cannula 128. In one embodiment, cannula 128 includes a needle hub 126 for engagement to distal end 132 of syringe barrel 124.

Proximal end 134 of syringe barrel 124 is generally open-ended, but is intended to be closed off and sealed to the external environment as discussed herein. Syringe barrel 124 may also include markings, such as graduations located on sidewall 130, for providing an indication as to the level or amount of fluid contained within interior chamber 136 of syringe barrel 124. Such markings may be provided on an external surface of sidewall 130, an internal surface of sidewall 130, or integrally formed or otherwise within sidewall 130 of syringe barrel 124. In other embodiments, alternatively, or in addition thereto, the markings may also provide a description of the contents of the syringe or other identifying information as may be known in the art, such as maximum and/or minimum fill lines.

Syringe 100 of the present disclosure may be a pre-filled syringe, and, therefore, may be provided for end use with a fluid, such as a medication or drug, contained within interior chamber 136 of syringe barrel 124, pre-filled by the manufacturer. In this manner, syringe 100 can be manufactured, pre-filled with a medication, sterilized, and packaged in packaging unit 14 for delivery, storage, and use by the end user. In such embodiments, syringe 100 may include a sealing member disposed at proximal end 134 of syringe barrel 124 to seal a fluid, such as a medication, within interior chamber 136 of syringe barrel 124.

In some embodiments, syringe barrel 124 may include a stopper which is moveably or slidably disposed within interior chamber 136, and in sealing contact with the internal surface of sidewall 130 of syringe barrel 124. The stopper may be sized relative to syringe barrel 124 to provide sealing engagement with the interior surface of sidewall 130 of syringe barrel 124. Additionally, the stopper may include one or more annular ribs extending around the periphery of the stopper to increase the sealing engagement between the stopper and the interior surface of sidewall 130 of syringe barrel 124. In alternate embodiments, a singular O-ring or a plurality of O-rings may be circumferentially disposed about the stopper to increase the sealing engagement with the interior surface of sidewall 130.

In other embodiments, a stopper may be engaged with a plunger rod 64 movably disposed within the injection device 16.

Referring to FIGS. 5A and 5B, syringe 100 includes a needle shield 102 which protectively surrounds and covers sharp tip 129 of cannula 128. In this manner, no portion of cannula 128 is exposed thereby significantly reducing the risk of accidental needle stick injuries. The needle shield 102 is engageable with a portion of packaging unit 14 to allow for automatic removal of the needle shield 102 of a respective pre-filled container 12 upon removal of the respective pre-filled container 12 from the packaging unit 14 as described in more detail below.

Figure 8:
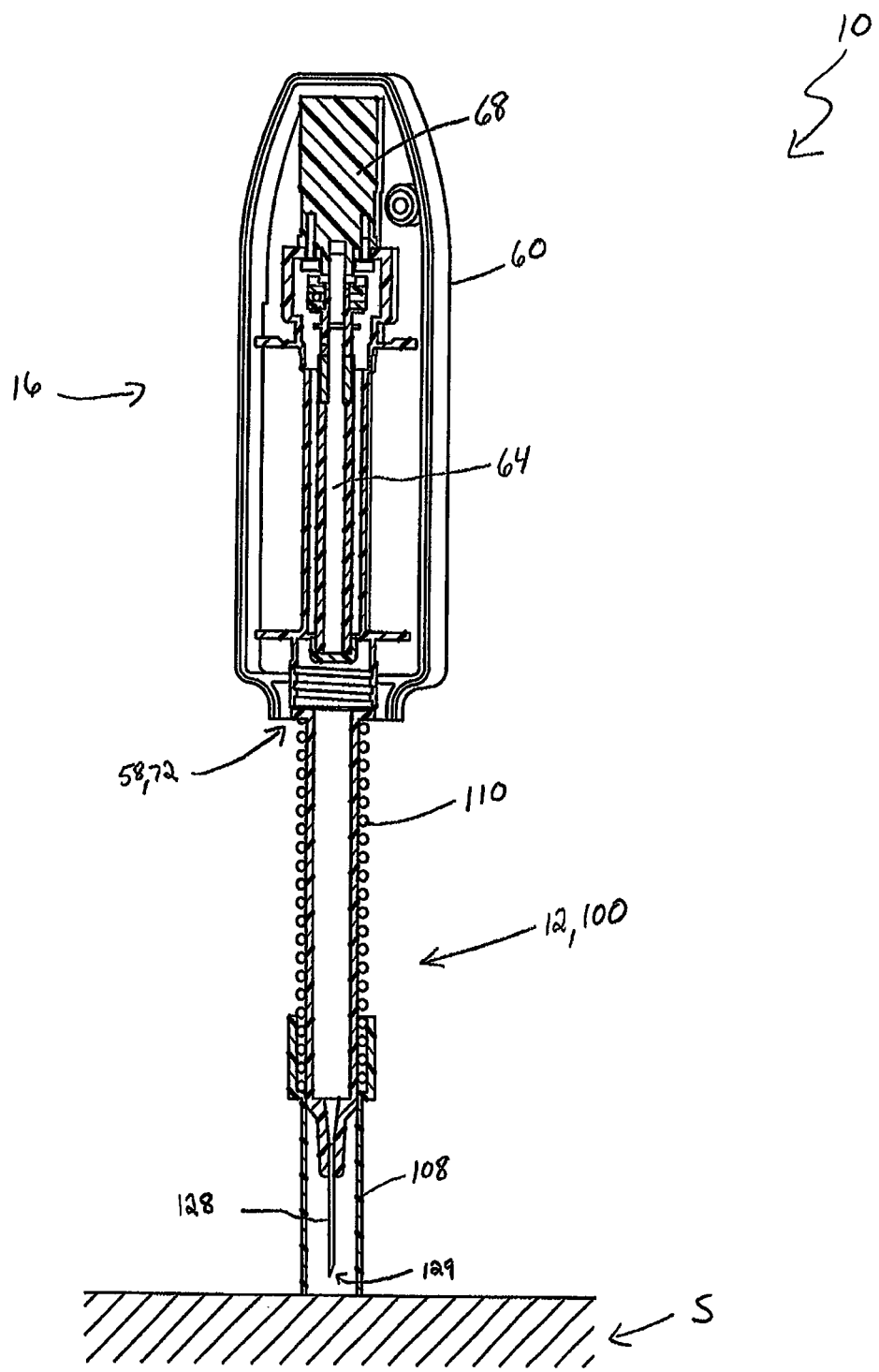
FIG. 8 is a cross-sectional view of an injection device of a drug storage and dispensing system engaged with a pre-filled container having a safety shield protectively surrounding a needle tip of the pre-filled container before an injection in accordance with an embodiment of the present invention.
Figure 9:
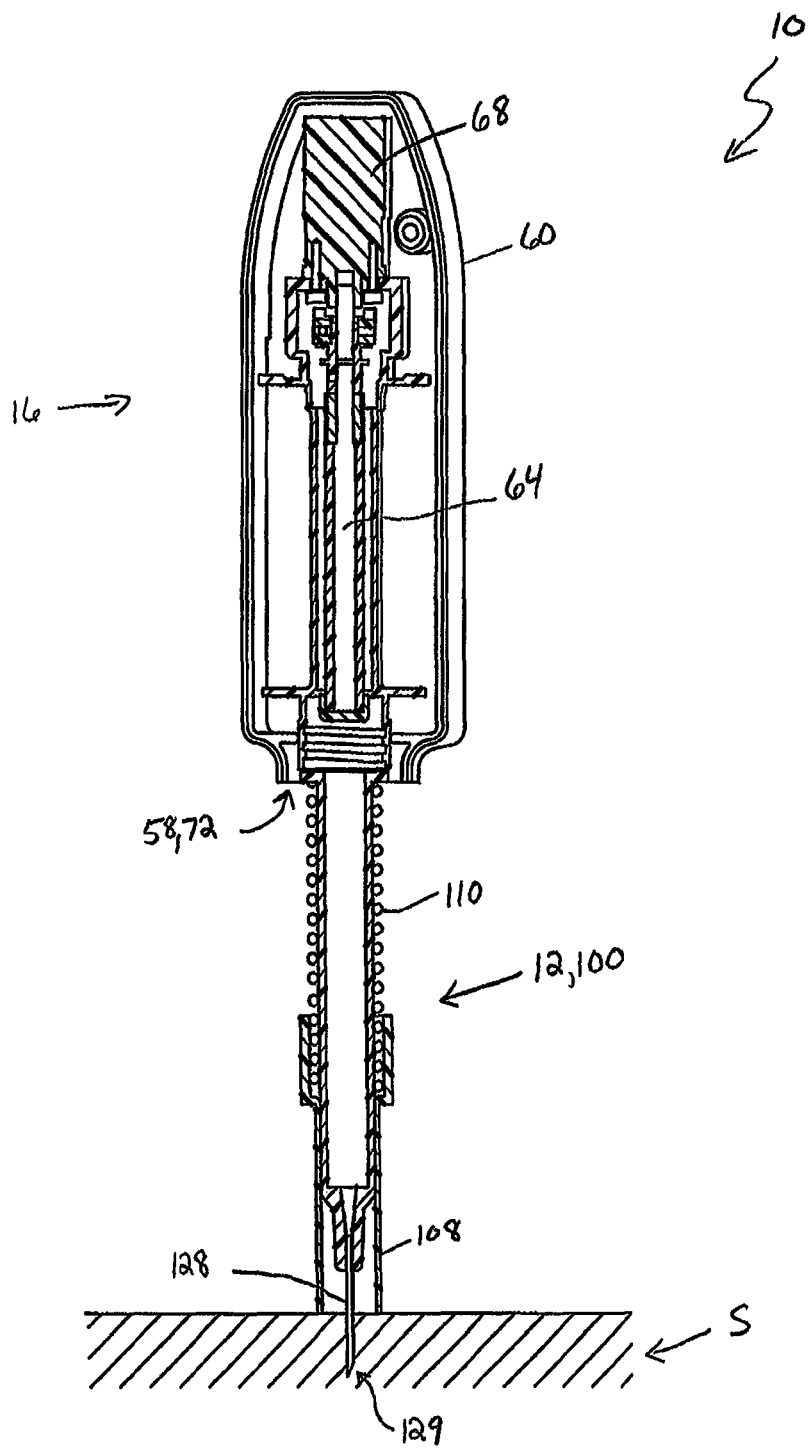
FIG. 9 is a cross-sectional view of an injection device of a drug storage and dispensing system engaged with a pre-filled container having a safety shield during an injection in accordance with an embodiment of the present invention.
Figure 10:
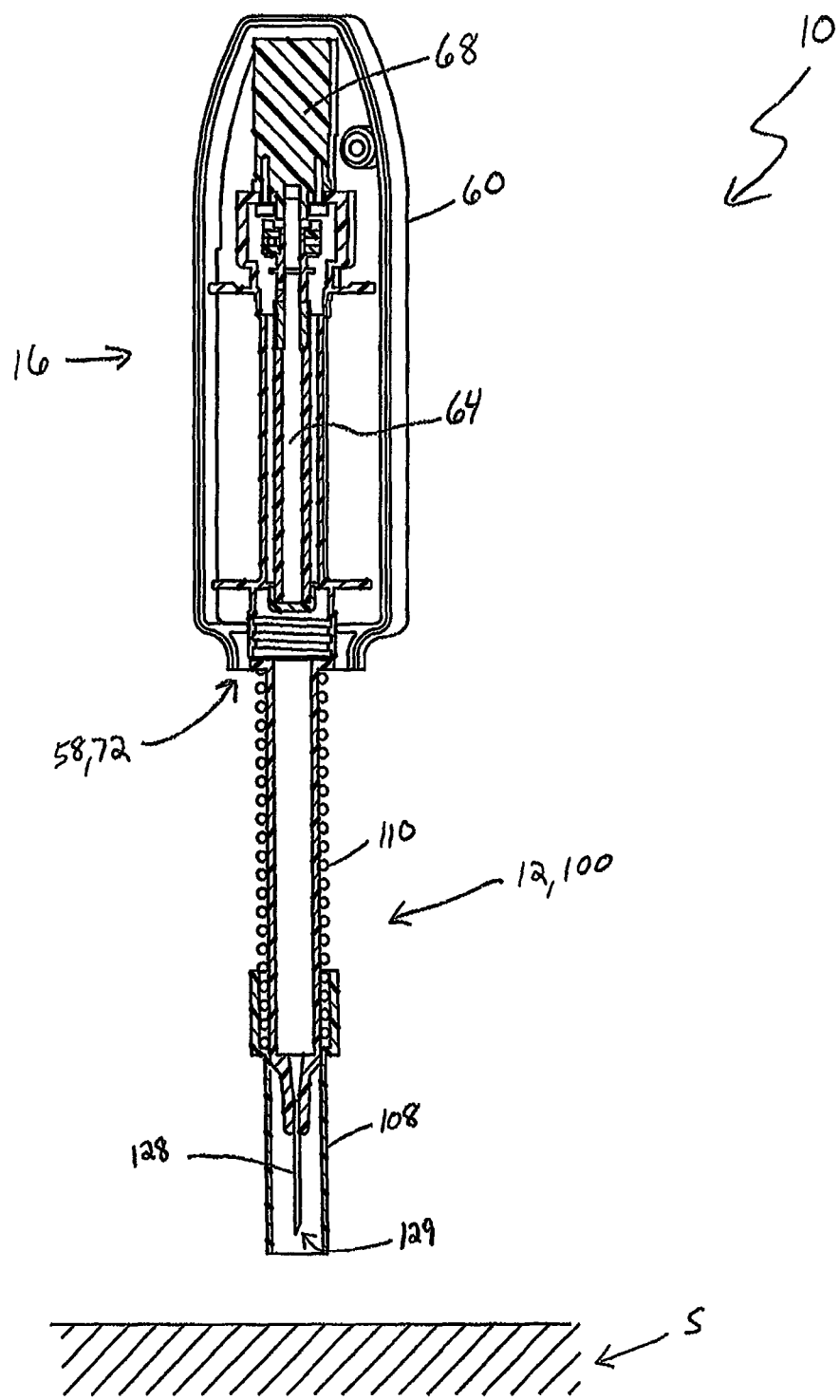
FIG. 10 is a cross-sectional view of an injection device of a drug storage and dispensing system engaged with a pre-filled container having a safety shield protectively surrounding a needle tip of the pre-filled container after an injection is completed in accordance with an embodiment of the present invention.
Figure 11:
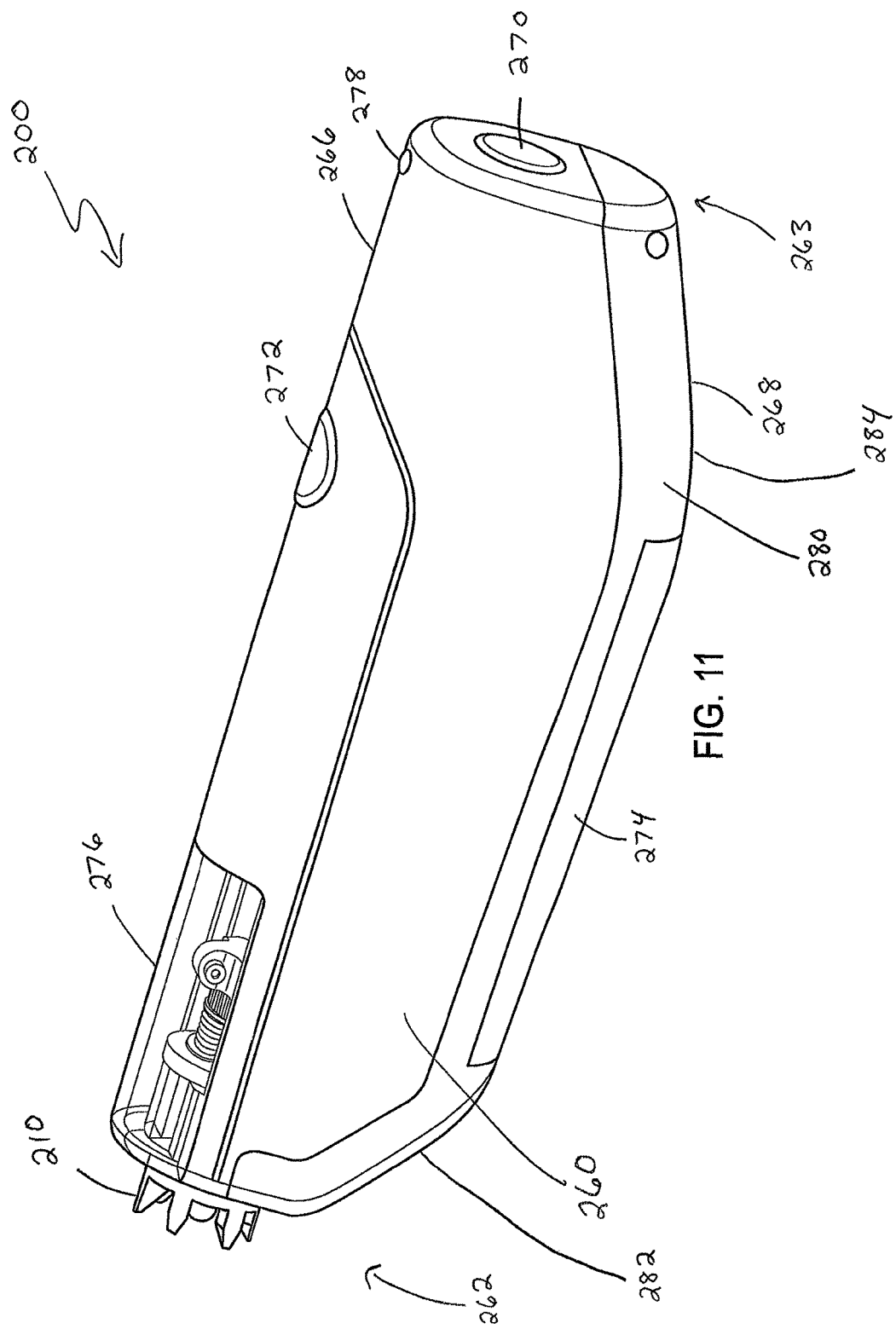
FIG. 11 is a perspective view of an injection device in accordance with an embodiment of the present invention.
Figure 12:
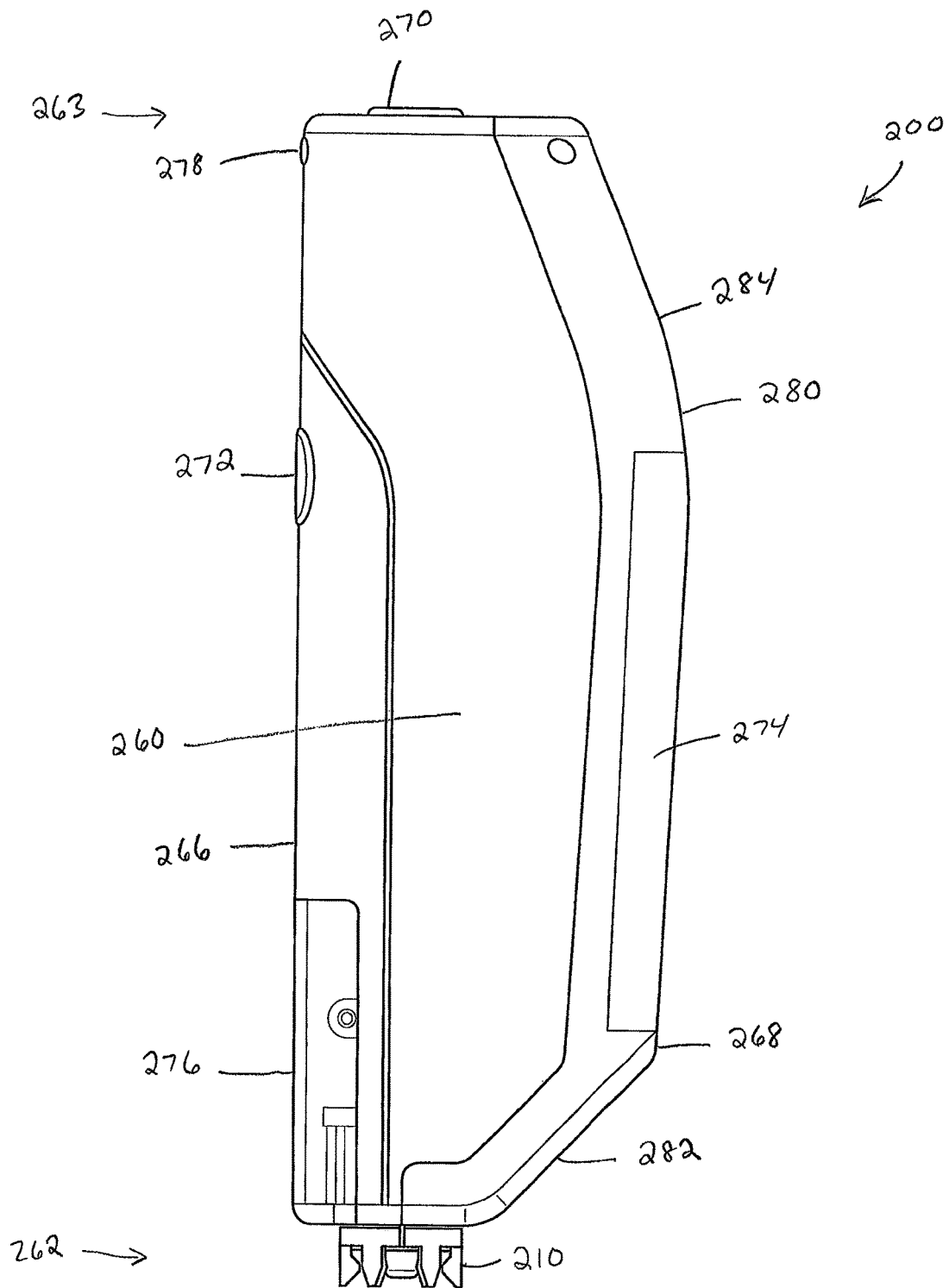
FIG. 12 is an elevation view of an injection device in accordance with an embodiment of the present invention.
Figure 13:
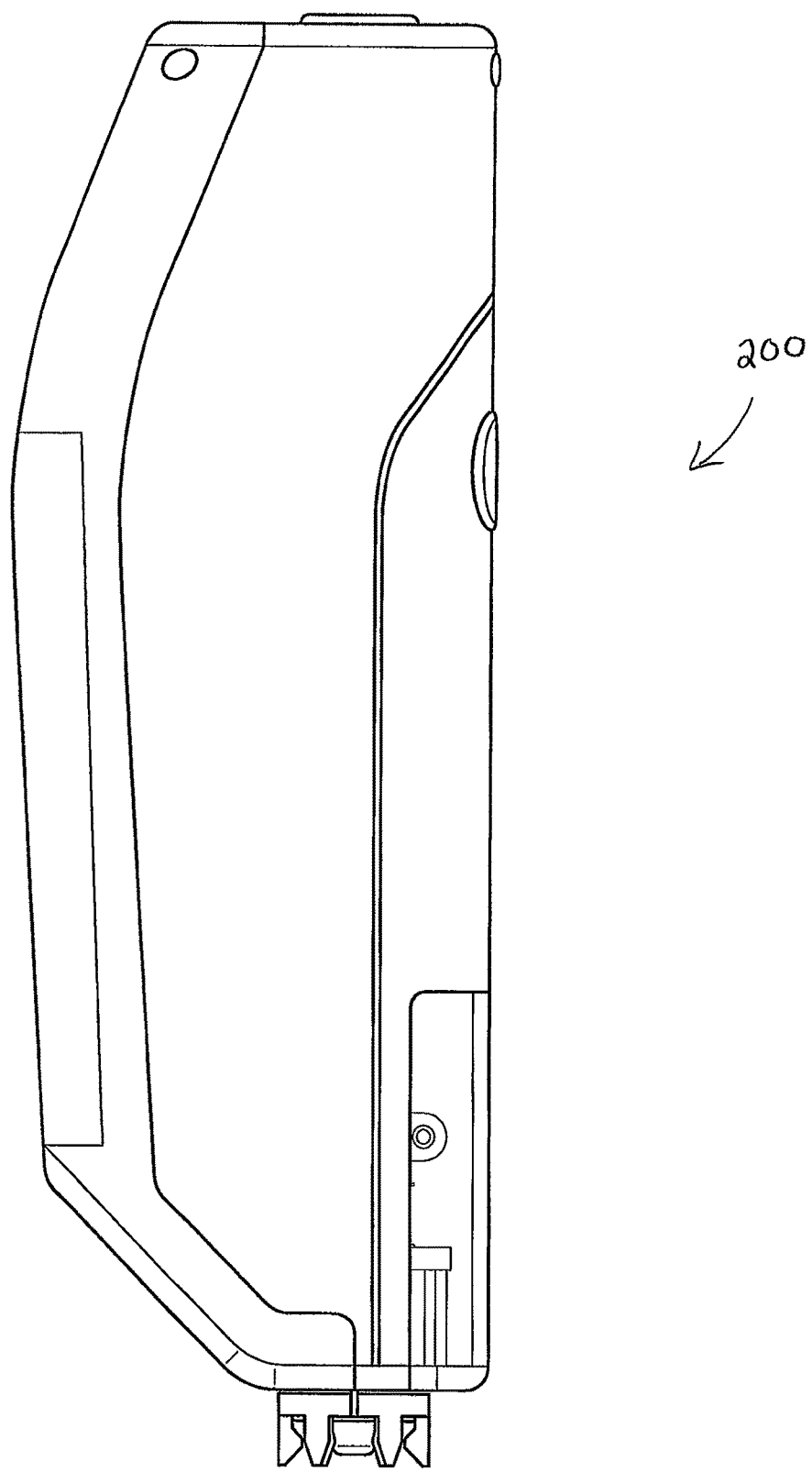
FIG. 13 is an elevation view of an injection device in accordance with an embodiment of the present invention.
Figure 14:
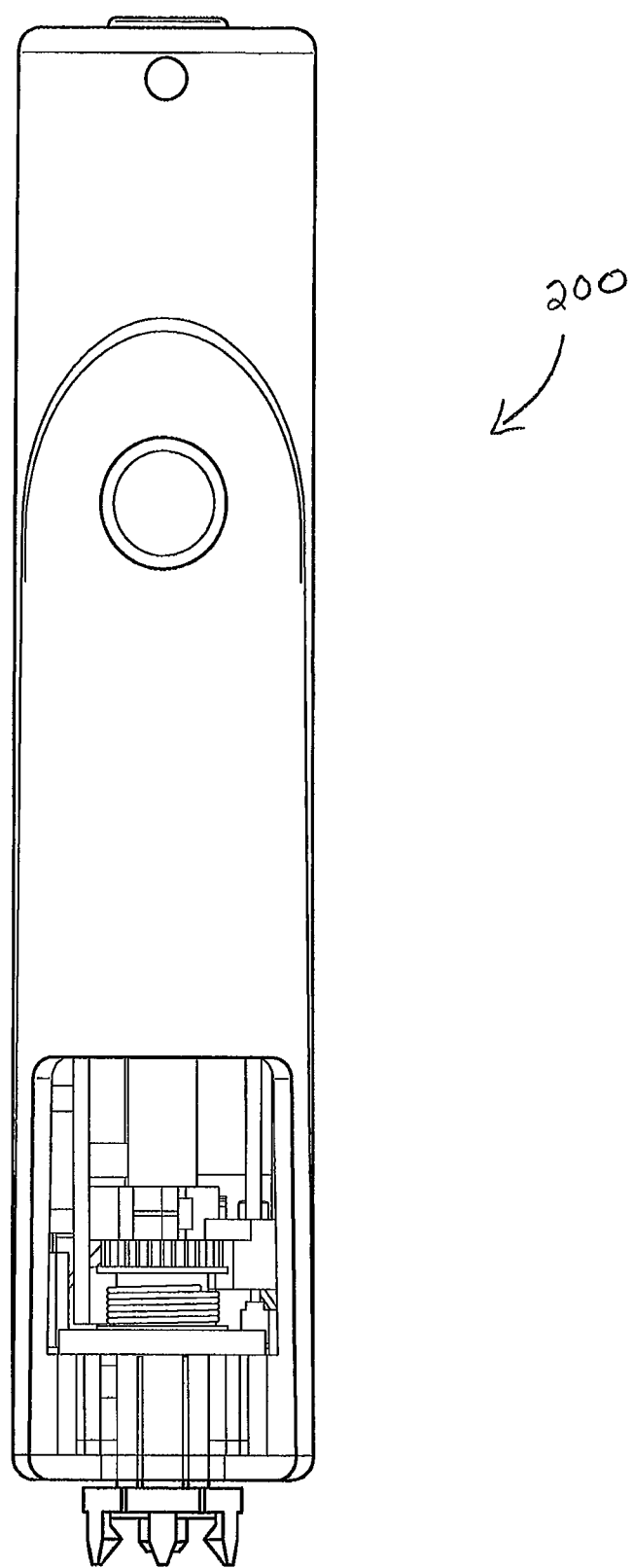
FIG. 14 is an elevation view of an injection device in accordance with an embodiment of the present invention.
Figure 15:
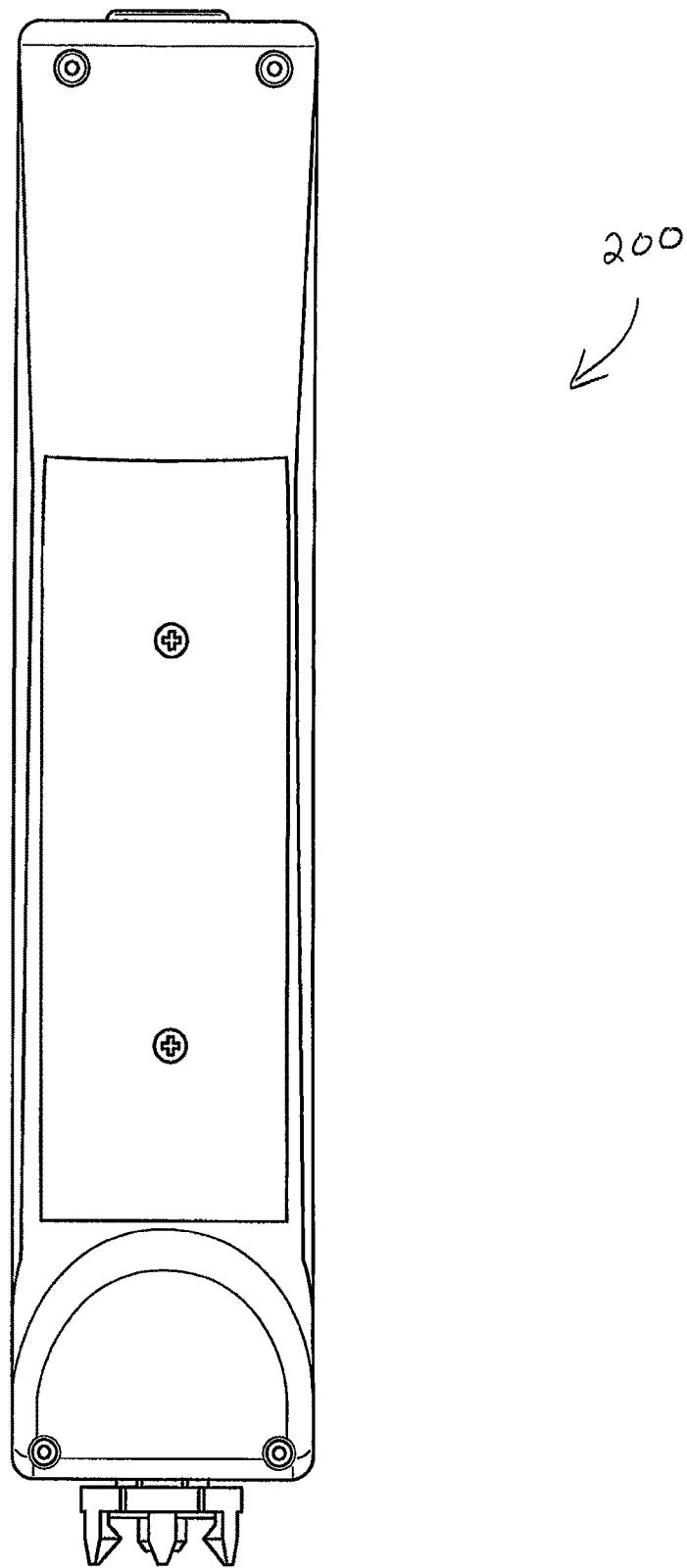
FIG. 15 is an elevation view of an injection device in accordance with an embodiment of the present invention.
Figure 16:
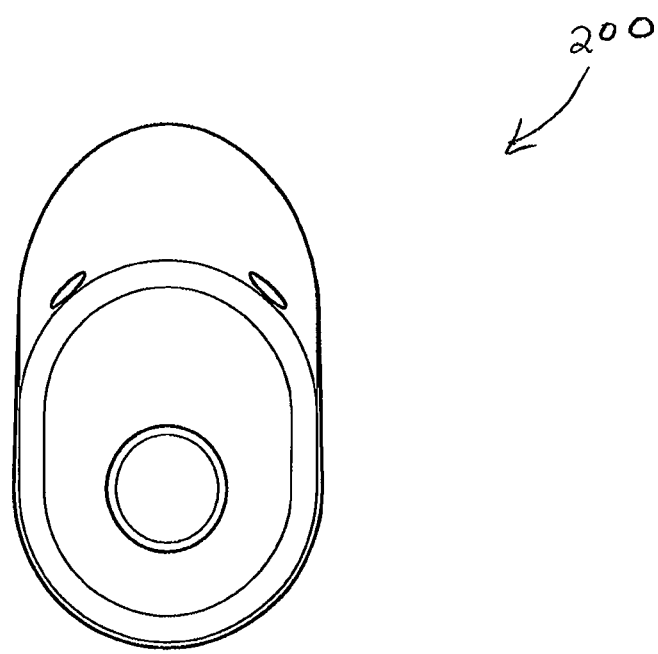
FIG. 16 is an elevation view of an injection device in accordance with an embodiment of the present invention.
Figure 17:
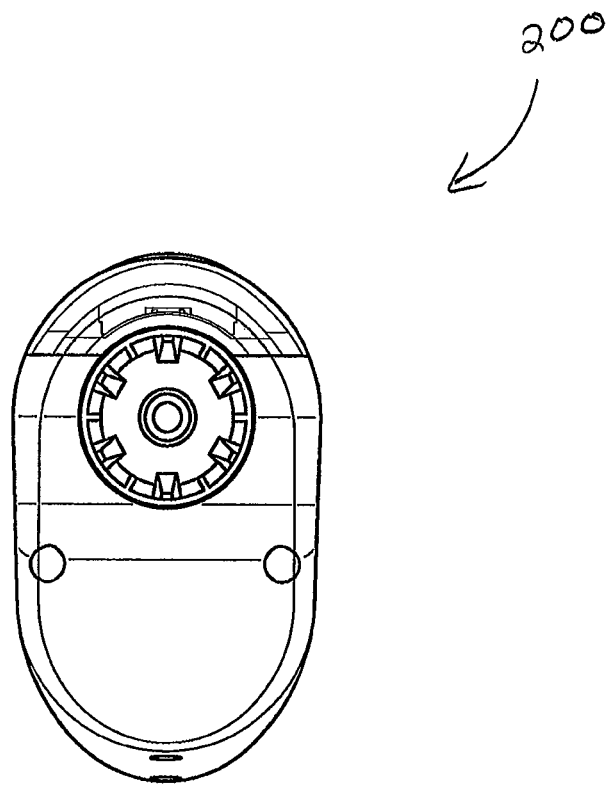
FIG. 17 is an elevation view of an injection device in accordance with an embodiment of the present invention.
Figure 18:
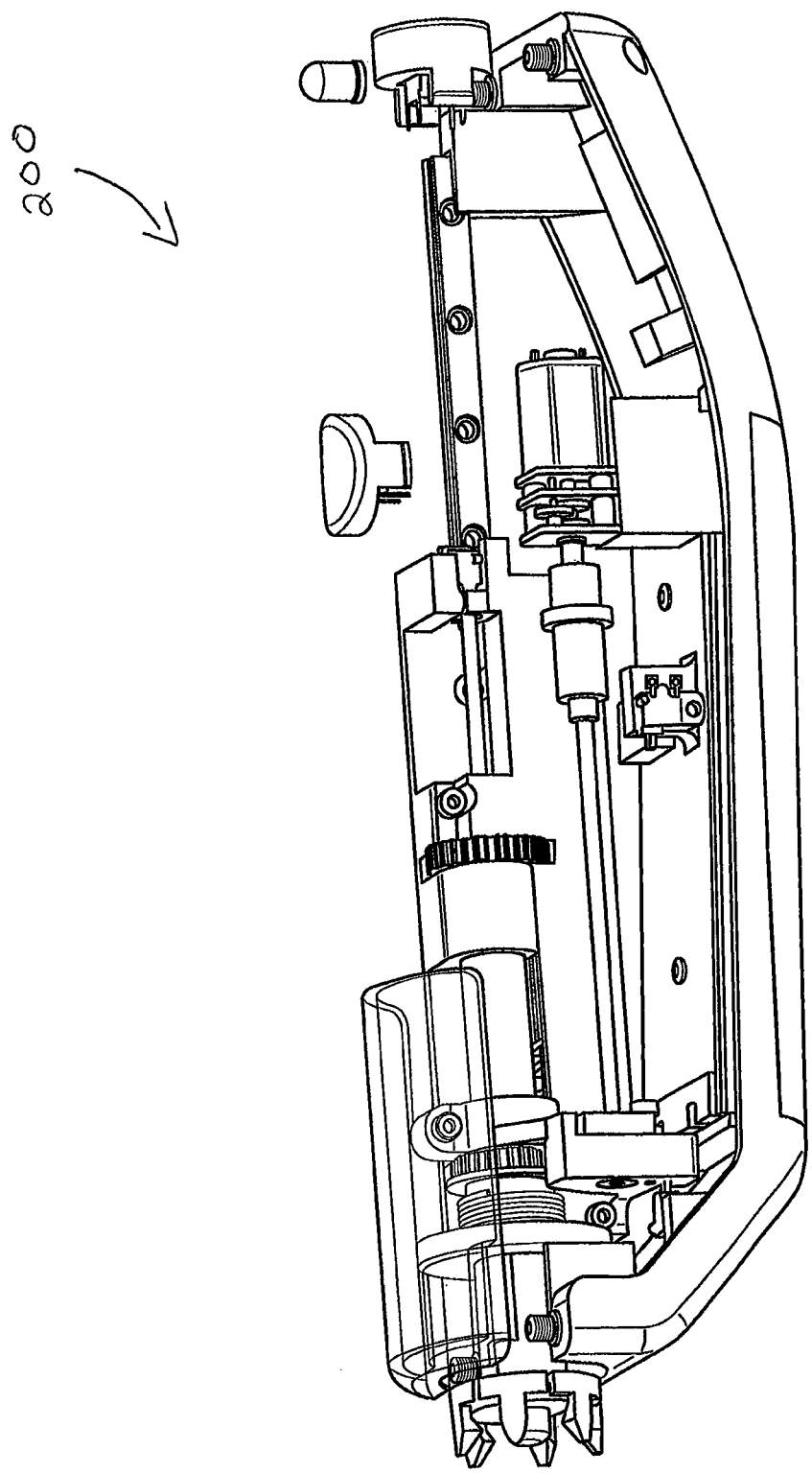
FIG. 18 is a perspective view of an injection device with a portion of a housing removed in accordance with an embodiment of the present invention.

The syringe 100 also includes a safety mechanism that is automatically triggered once an injection is completed so that the sharp tip 129 of the cannula 128 cannot be accessed, thus preventing needle-associated injuries. In one embodiment, the safety mechanism is a part of the syringe 100. For example, referring to FIGS. 5B and 8-10, syringe 100 includes a safety shield 108 which is coupled to the syringe 100 and is adapted to automatically shield a sharp tip 129 of cannula 128 of a respective pre-filled container after an injection is completed. The safety shield 108 protectively surrounds and covers sharp tip 129 of cannula 128. In this manner, no portion of cannula 128 is exposed thereby significantly reducing the risk of accidental needle stick injuries. In one embodiment, the safety shield 108 is engaged with a spring 110. In this manner, as the sharp tip 129 of cannula 128 is removed from a skin surface S of a patient, the spring 110 exerts a biasing force on the safety shield 108 to move the safety shield 108 to protectively surround and cover sharp tip 129 of cannula 128 simultaneously with the cannula 128 exiting the skin surface S of the patient as shown in FIGS. 8-10.

In another embodiment, the safety mechanism may be a part of the injection device 16.

In one embodiment, each of the pre-filled containers 12 includes a readable information portion. In one embodiment, at least a part of the readable information portion is a barcode. In other embodiments, the readable information portion may include any unique identifier, such as but not limited to, a bar code, QR code, datamatrix, radiofrequency identification (RFID) tag, or other identifier. For example, in one embodiment, at least a part of the readable information portion is an RFID tag. An RFID tag may contain an integrated circuit chip that can provide information such as a container identification number, temperature information, detection of shock or abuse, or similar information. In some embodiments, readable information portions may be placed on a portion of the packaging unit 14.

The injection device 16 may include a scanner portion adapted to read the readable information portion of respective pre-filled containers 12. In this manner, the injection device 16 is able to read the information contained therein, e.g., type of drug, lot number, expiration date, or other identifying information of the pre-filled container 12, and either store it in its on-board non-volatile memory, or transmit it to a nearby smartphone or to a distant data management system. Similarly, prefilled containers 12 may be equipped with sensors such as temperature/humidity or shock/abuse sensors. Signals from those sensors can be read by the injection device 16 upon pick-up. If an abnormal condition is detected, an indicator present on the injection device 16 will alert the user and an optional interlock can prevent from proceeding with the injection. Once the syringe 100 is picked-up and no abnormal container condition is detected, the healthcare worker proceeds with the injection.

The drug storage and dispensing system 10 may also include a data management platform that stores and processes the data transmitted from the injection device.

The packaging unit 14 of the drug storage and dispensing system 10 provides for drug storage and administration while minimizing the space occupied by such containers in the cold chain and minimizes the risk of a needle-stick injury, as a healthcare worker does not have to manually remove the needle shield 102 when removing a pre-filled container 12 from the packaging unit 14. In this manner, the packaging unit 14 provides for a productivity and efficiency gain in mass immunization campaigns.

Figure 2:
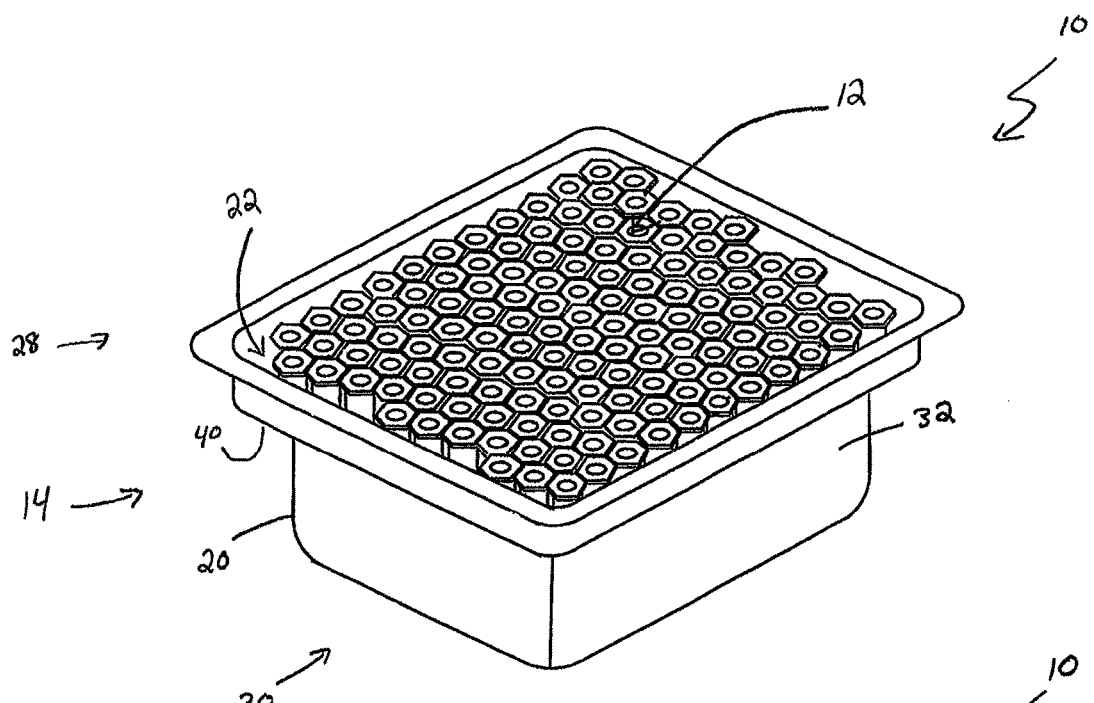
FIG. 2 is an assembled, perspective view of a packaging unit of a drug storage and dispensing system for a plurality of pre-filled containers in accordance with an embodiment of the present invention.
Figure 3:
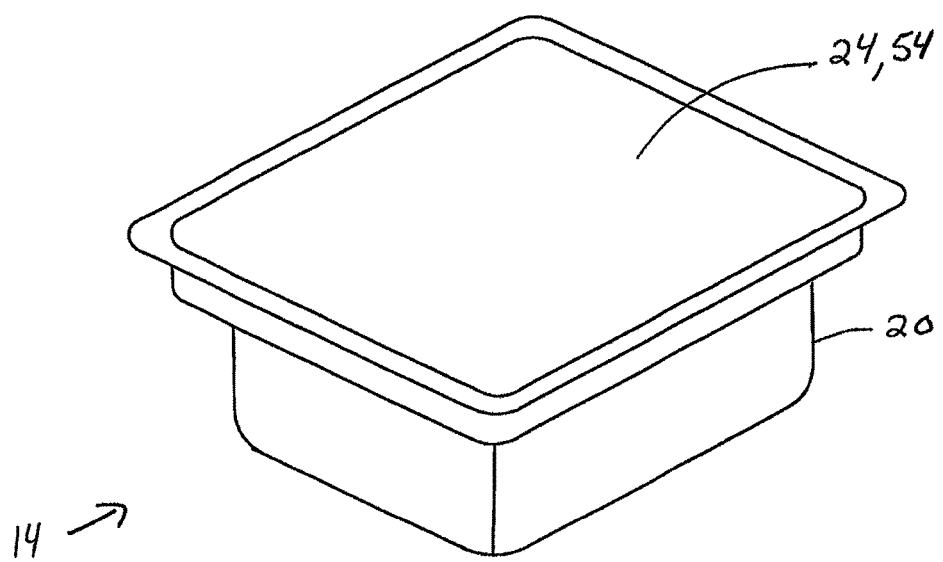
FIG. 3 is an assembled, perspective view of a packaging unit of a drug storage and dispensing system for a plurality of pre-filled containers with a sealing member secured to the packaging unit in accordance with an embodiment of the present invention.

Referring to FIGS. 1-3, the packaging unit 14 includes a tub member 20, a nest member 22, and a sealing member 24. The tub member 20 defines a receiving cavity 26 that is sized and adapted to receive the plurality of pre-filled containers 12 therein. The tub member 20 generally includes a first or top end 28, a second or bottom end 30, and a sidewall 32 extending between top end 28 and bottom end 30. Sidewall 32 defines the receiving cavity 26 of tub member 20.

Referring to FIG. 1, tub member 20 includes a locking lip 34 at top end 28. Disposed below locking lip 34 is an upper tray portion 36 having a cross-section that has a greater area than a cross-section disposed below upper tray portion 36, i.e., a receiving cavity portion 38, such that a shoulder 40 is defined therebetween. Upper tray portion 36 receives and supports nest member 22 as will be described in more detail below.

The nest member 22 generally includes a nest plate 42 having a superior surface 44 and an inferior surface 46 and a plurality of container holding portions 48 adapted to receive respective pre-filled containers 12 therein. The nest member 22 is securable within the tub member 20 such that nest plate 42 abuts upper tray portion 36 of tub member 20 as shown in FIG. 2. Each of the container holding portions 48 includes an engagement member 50 (FIGS. 7A and 7B) adapted to automatically remove the needle shield 102 of a respective pre-filled container 12 upon removal of the respective pre-filled container 12 from the container holding portion 48 of the packaging unit 14.

Referring to FIGS. 7A and 7B, in one embodiment, the engagement member 50 comprises a plurality of elastically deformable fins 52. The deformable fins 52 allow for automatic removal of a needle shield 102 of a respective pre-filled container 12 upon removal of the respective pre-filled container 12 from the container holding portion 48 of the packaging unit 14. With a respective pre-filled container 12 placed within a respective container holding portion 48 of the packaging unit 14, the deformable fins 52 engage within the opening 106 of the needle shield 102 of the pre-filled container 12 as shown in FIG. 7B. In this manner, the pre-filled container 12 is secured within the container holding portion 48 of the packaging unit 14. Also, the engagement of the deformable fins 52 within the opening 106 of the needle shield 102 allows for automatic removal of the needle shield 102 when the pre-filled container 12 is removed from a respective container holding portion 48 of the packaging unit 14. When the pre-filled container 12 is removed from the packaging unit 14, the needle shield 102 is automatically removed from the pre-filled container 12 via the deformable fins 52 and retained within the container holding portion 48. In this manner, the packaging unit 14 minimizes the risk of a needle-stick injury, as a healthcare worker does not have to manually remove the needle shield 102 when removing a pre-filled container 12 from the packaging unit 14.

Sealing member 24 is removably securable to tub member 20 and provides a mechanism to securely seal and protect the plurality of pre-filled containers 12 within tub member 20 of packaging unit 14. In one embodiment, the sealing member 24 comprises a cover 54 (FIG. 3).

The packaging unit 14 may include a temperature control unit. In one embodiment, the packaging unit 14 may have a temperature control unit specifically designed to fit a single tub member 20. This type of temperature control unit may be used together with the tub to limit (either passively or actively) temperature excursions for the pre-filled drug containers 12 inside the tub member 20. This type of temperature control unit may be best used when the drug storage and dispensing system 10 is used outside of a traditional healthcare setting.

In another embodiment, the packaging unit 14 may have a temperature control unit specifically designed to fit multiple tub members 20. This type of temperature control unit is used to store multiple tub members 20 in a temperature controlled environment. This temperature control unit may be best used when the drug storage and dispensing system 10 is used in a traditional healthcare setting.

The drug storage and dispensing system 10 of the present disclosure can be used either in a traditional healthcare setting or outside of a traditional healthcare setting to deliver drugs on demand in a safe and quick manner. The drug storage and dispensing system 10 can also be used by patients suffering from chronic diseases who self-administer their injectable medication.

The injection device 16 of the drug storage and dispensing system 10 provides for a smart injection assist device that is used to perform drug administration together with a pre-filled drug container 12. The injection device 16 allows for automatic injection of the medication from respective pre-filled containers 12 and includes an engagement portion 58 (FIGS. 6 and 8-10) adapted to be removably engageable to each of the respective pre-filled containers 12. With the injection device 16 engaged with a respective pre-filled container 12, the injection device 16 is adapted to automatically actuate a plunger rod 64 to expel the medication from the respective pre-filled container 12. Such automatic actuation can be accomplished by means of either a mechanical or electromechanical actuator residing in the injection device 16. For example, an electric motor 68 (FIGS. 6 and 8-10) may be used.

Referring to FIGS. 6 and 8-10, the injection device 16 includes a housing 60 having a first end 62 and a second end 63, a plunger rod 64 movably disposed within the housing 60 of the injection device 16, a lead screw 66, an electric motor 68, a rigid axial coupler 70, and an engagement portion 58 adapted to be removably engageable to each of the respective pre-filled containers 12. In one embodiment, the engagement portion 58 comprises a locking member 72 that secures a portion of a pre-filled container 12 to the injection device 16. In another embodiment, the engagement portion 58 comprises a threaded portion that secures a portion of a pre-filled container 12 to the injection device 16. In one embodiment, the plunger rod 64 may include a threaded portion 74. In one embodiment, the injection device 16 may include a scanner portion adapted to read the readable information portion of respective pre-filled containers 12 as described above.

The plunger rod 64 may be attached to the injection device 16 and movably disposed within the injection device 16. The plunger rod 64 may be permanently attached to the injection device 16 or may be inserted in the injection device 16 by a healthcare worker before each syringe pick-up. In use, a healthcare worker may secure or snap the injection device 16 onto a selected syringe 100 and activate the injection device 16 by pushing an actuation button that deploys the plunger rod 64 and secures or screws it to a portion of the syringe 100. In some embodiments, the plunger rod 64 may be a reusable part. In other embodiments, the plunger rod 64 may be a disposable part.

The injection device 16 is a smart device and can capture, store, and transmit information about its usage. The injection device 16 is equipped with an on-board electronic module comprising a non-volatile memory that can record and store container unique identification information, as well as time stamping information relative to the usage of the pre-filled container 12. The injection device electronic module is also equipped with a global positioning system (GPS) receiver that can record and store latitude and longitude coordinates of usage location. When used indoor, the injection device electronic module is compatible with existing indoor positioning systems using triangulation from wireless signal receivers.

The injection device electronic module is also equipped with a wireless communication module able to establish distant communication by way of one or several of the following methods: near field communication (NFC), Bluetooth low energy (BLE), Wi-Fi, ZigBee, and/or GSM. The injection device electronic module comprises an embedded piece of software which can encrypt the collected information prior to its transmission. The information collected by the injection device can therefore be securely transmitted to a distant recipient by any of the above means. Examples of recipients are: a smartphone, a tablet, and/or a data management platform. In order to visualize transmitted data, application software is developed for all of the above hardware platforms. In case the information is sent to a distant data management platform, the visualization can happen either on a smartphone, a tablet, or a web portal that can also be accessed from an internet-connected computer.

In one embodiment, the injection device could incorporate a motorized-darting mechanism that inserts the selected syringe 100 into the skin surface of a patient at the right pre-set depth. The pre-set depth of insertion is derived from reading the syringe identifier that bears information on the type of injection associated with the syringe.

Referring to FIGS. 1-10, the use of drug storage and dispensing system 10 will now be described.

Referring to FIGS. 1-3, a healthcare worker ready to administer a treatment may first peel off a sealing member 24 of the packaging unit 14 to expose pre-filled drug containers 12. The injection device 16 may then be used to pick-up and remove an individual pre-filled container 12, e.g., a pre-filled syringe 100. During removal of the pre-filled container 12 from the container holding portion 48 of the packaging unit 14, the deformable fins 52 of the nest member 22 of the packaging unit 14 allow for automatic removal of a needle shield 102 of a respective pre-filled container 12. In this manner, the packaging unit 14 allows for the needle shield 102 to be automatically removed and may remain inside the nest member 22 when picking up the pre-filled container 12, e.g., syringe 100.

As discussed above, the plunger rod 64 is attached to the injection device 16. In use, a healthcare worker may secure or snap the injection device 16 onto a selected syringe 100 and activate the injection device 16 by pushing an actuation button that deploys the plunger rod 64 and secures or screws it to a portion of the syringe 100. The healthcare worker may then remove the selected syringe 100 from the tub member 20 of the packaging unit 14 and proceed with the injection. As previously discussed, the needle shield 102 is automatically removed and remains inside the nest member 22 when removing the selected syringe 100 from the packaging unit 14.

As discussed above, the syringe may include a unique identifier that the injection device 16 can read the information contained therein and either store it in its on-board non-volatile memory, or transmit it to a nearby smartphone or to a distant data management system. Similarly, prefilled containers may be equipped with sensors such as temperature/humidity or shock/abuse sensors. Signals from those sensors can be read by the injection device 16 upon pick-up. If an abnormal condition is detected, an indicator present on the injection device 16 will alert the user and an optional interlock can prevent from proceeding with the injection. Once the syringe is picked-up and no abnormal container condition is detected, the healthcare worker proceeds with the injection using the injection device 16.

As described above, the injection device 16 allows for automatic injection of the medication from a selected pre-filled container 12. With the injection device 16 engaged with a respective pre-filled container 12, the injection device 16 is adapted to automatically actuate a plunger rod 64 to expel the medication from the respective pre-filled container 12.

The injection completion can optionally be sensed by the injection device 16, and the corresponding event can either be stored in its on-board non-volatile memory or transmitted to a nearby smartphone or to a distant data management system.

Once injection is completed, a safety mechanism is triggered so that the sharp tip 129 of the cannula 128 cannot be accessed, thus preventing needle-associated injuries. For example, referring to FIGS. 8-10, the safety shield 108 is adapted to automatically shield a needle tip, e.g., sharp tip 129 of cannula 128, of a respective pre-filled container 12 after an injection is completed.

The drug storage and dispensing system 10 of the present disclosure can be used either in a traditional healthcare setting or outside of a traditional healthcare setting to deliver drugs on demand in a safe and quick manner. The drug storage and dispensing system 10 can also be used by patients suffering from chronic diseases who self-administer their injectable medication.

The drug storage and dispensing system 10 of the present disclosure is especially useful when used to perform vaccinations. Vaccination campaigns can be performed in a traditional healthcare setting, e.g., a doctor's office, hospitals, clinics, minute clinics, pharmacies, vaccination center, or similar settings, or in non-traditional settings, e.g., retail outlets such as supermarkets, schools, or offices, or in no particular setting and directly in contact with the targeted population as it is often the case in developing countries.

Pandemic situations require a medical practitioner to be able to vaccinate a large number of people in a very short amount of time. In all non-traditional vaccination settings, the drug storage and dispensing system 10 of the present disclosure is especially useful for the following reasons: (1) the drug storage and dispensing system 10 provides a faster and safe way of vaccinating more people per unit of time; (2) the drug storage and dispensing system 10 provides a means to optimize cold chain space by offering a denser packaging compared to other packaging systems for pre-filled containers; and (3) the drug storage and dispensing system 10 provides an automated capture and real-time transmission of vaccination data, thus enabling the precise tracking of vaccination coverage at a population level or accurate information in an individual vaccination log or electronic medical record at an individual level.

The drug storage and dispensing system 10 is envisioned to be a part of a novel service of an on-demand, mobile vaccination system. People wishing to be vaccinated can place their order online after responding to a short questionnaire on their current health status. Dispatching units that may be housed in nearby pharmacies would then prepare and group orders coming from their area of responsibility. Orders could then be loaded on a van or truck driven by a healthcare worker who goes on a vaccine delivery. A delivery itinerary and schedule could be optimized by a specific software and updated on-the-fly to account for any last minute change requests by a customer.

FIGS. 11-50B illustrate another exemplary embodiment of an injection device 200 of the present disclosure. The injection device 200 provides a novel way of auto-disabling a container 12, such as a syringe 100, as a plunger rod is not engaged with the container 12 until the container 12 is actually used.

The injection device 200 of the drug storage and dispensing system 10 provides for a smart injection assist device that is used to perform drug administration together with a pre-filled drug container 12. The injection device 200 allows for automatic injection of the medication from respective pre-filled containers 12 and includes an engagement assembly 210 adapted to be removably engageable to each of the respective pre-filled containers 12. With the injection device 200 engaged with a respective pre-filled container 12, the injection device 200 is adapted to automatically actuate a plunger rod 264 to expel the medication from the respective pre-filled container 12. Such automatic actuation can be accomplished by means of either a mechanical or electromechanical actuator residing in the injection device 200. For example, an electric motor 268 (FIG. 42) may be used.

Referring to FIGS. 11-50B, the injection device 200 includes an engagement assembly 210, a retraction assembly 212, a locking assembly 214, a scan assembly 216, a rotation assembly 218, an actuator assembly 220, and an ejection assembly 222.

Referring to FIGS. 11-26, the injection device 200 includes a housing 260 having a first end 262 and a second end 263, a plunger rod 264 movably disposed within the housing 260 of the injection device 200, a top or first button 270, a side or second button 272, a battery compartment 274 (FIG. 38), a transparent window 276, an indicator portion 278, a gripping portion 280, an angled portion 282, and a bottom contour 284.

In one embodiment, the housing 260 may include a top housing portion 266 and a bottom housing portion 268. The top housing portion 266 may be removably securable to the bottom housing portion 268.

In one embodiment, the top or first button 270 is a container retract and/or eject button on the back end, e.g., the second end 263, of the injection device 200. In this manner, the location of the first button 270 is ideal for preventing unintentional actuation of the first button 270. In one embodiment, the side or second button 272 is an injection button.

Figure 25:
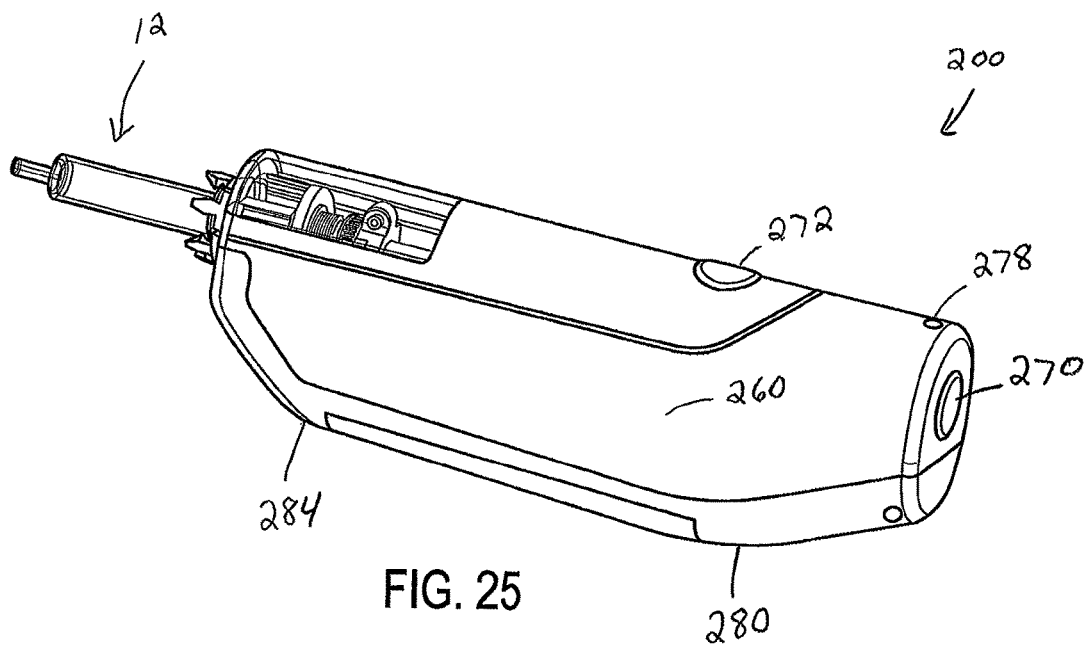
FIG. 25 is a perspective view of an injection device in accordance with an embodiment of the present invention.
Figure 26:
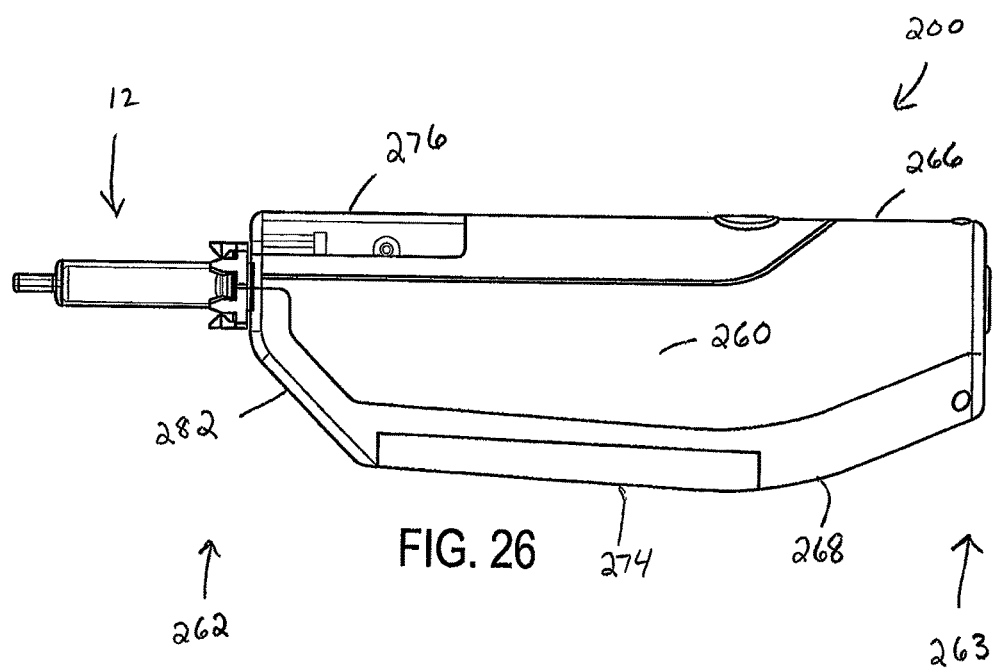
FIG. 26 is an elevation view of an injection device in accordance with an embodiment of the present invention.
Figure 31:
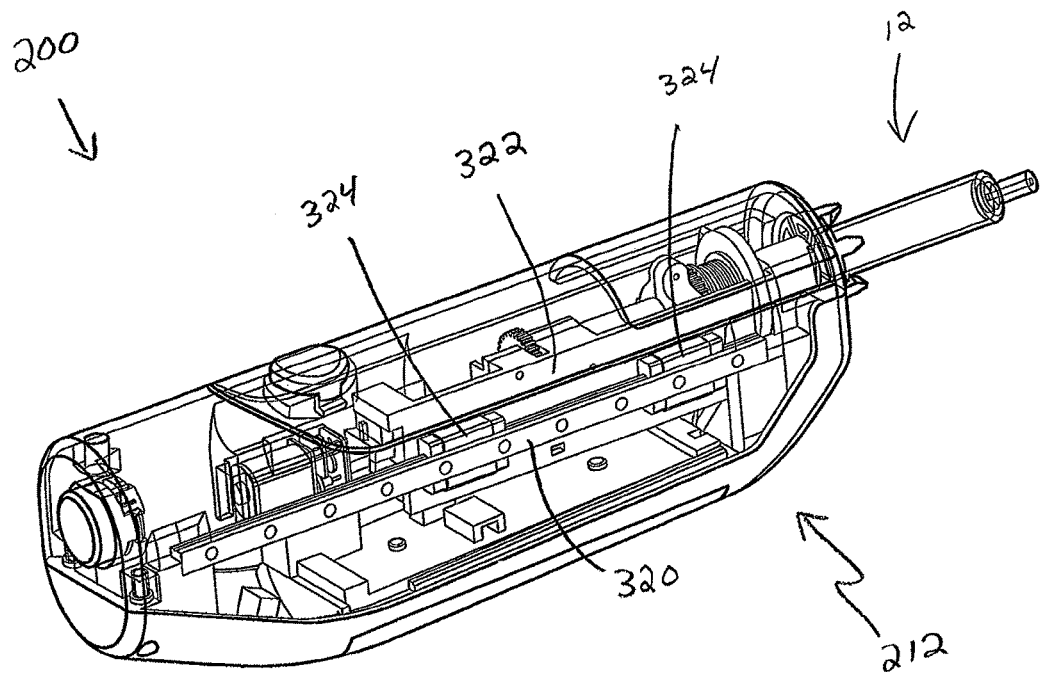
FIG. 31 is a perspective view of an injection device in a first position with a housing hidden to illustrate a retraction assembly in accordance with an embodiment of the present invention.
Figure 32:
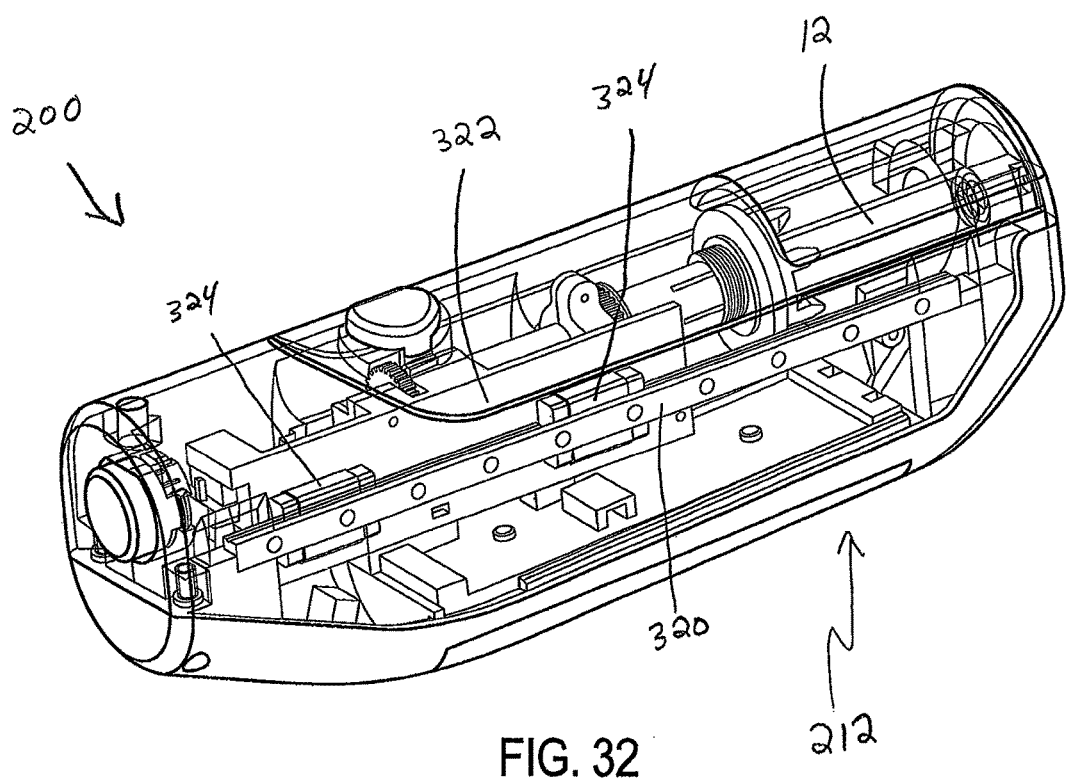
FIG. 32 is a perspective view of an injection device in a second position with a housing hidden to illustrate a retraction assembly in accordance with an embodiment of the present invention.
Figure 33:
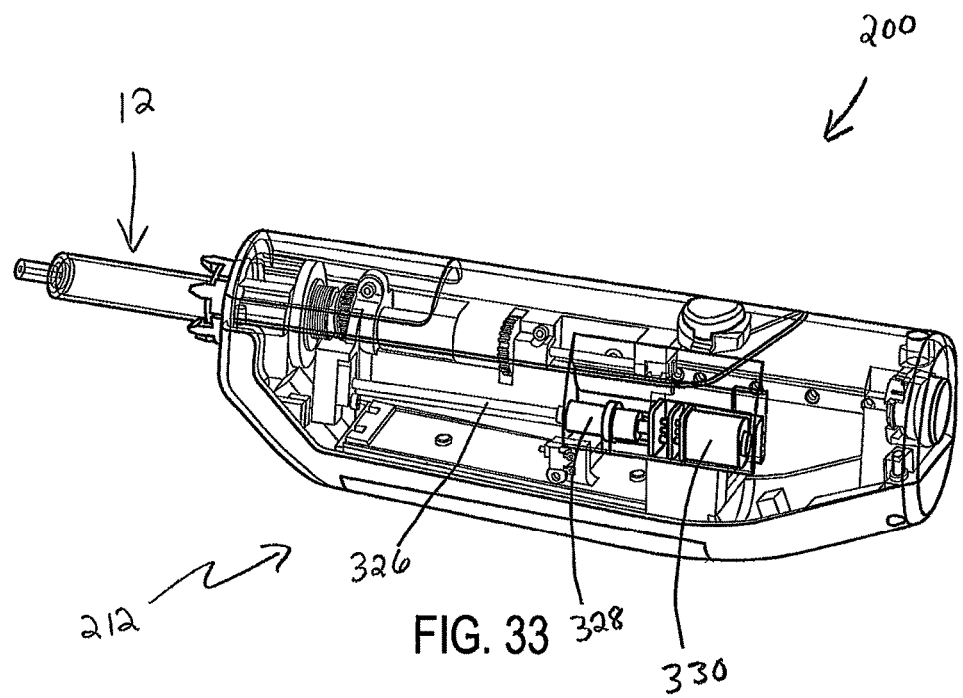
FIG. 33 is a perspective view of an injection device in a first position with a housing hidden to illustrate a retraction assembly in accordance with an embodiment of the present invention.
Figure 34:
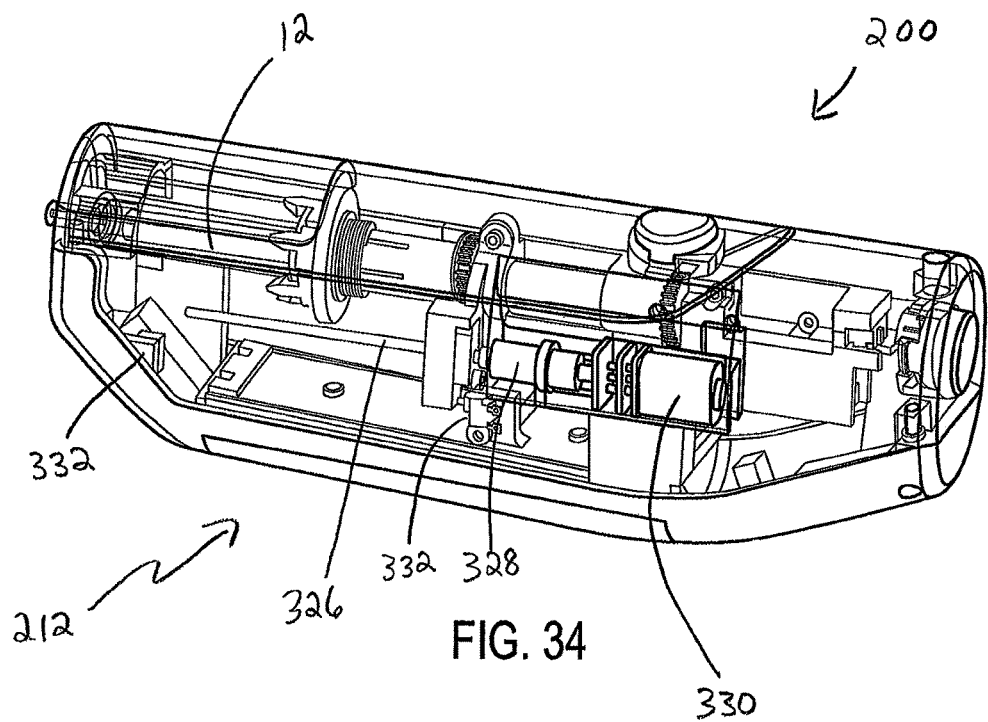
FIG. 34 is a perspective view of an injection device in a second position with a housing hidden to illustrate a retraction assembly in accordance with an embodiment of the present invention.

Referring to FIGS. 25 and 26, the transparent window 276 provides a user with a viewing window to view a container 12 within the injection device 200 before injection. In one embodiment, the indicator portion 278 comprises an LED to indicate to a user the injector status. In one embodiment, the injection device 200 includes a gripping portion 280 that provides an easy to grip surface and configuration for a user of the injection device 200. For example, in one embodiment, the gripping portion 280 includes an overmolded rubber or soft touch bottom for an enhanced grip for a user of the injection device 200. In one embodiment, the injection device 200 includes an angled portion 282 at a front end, e.g., the first end 262, to allow a better view and/or less obstructed view of an injection site during injection. In one embodiment, the injection device 200 includes a bottom contour 284 that is designed to match a shape of a hand of a user gripping the injection device 200 during injection.

Figure 38:
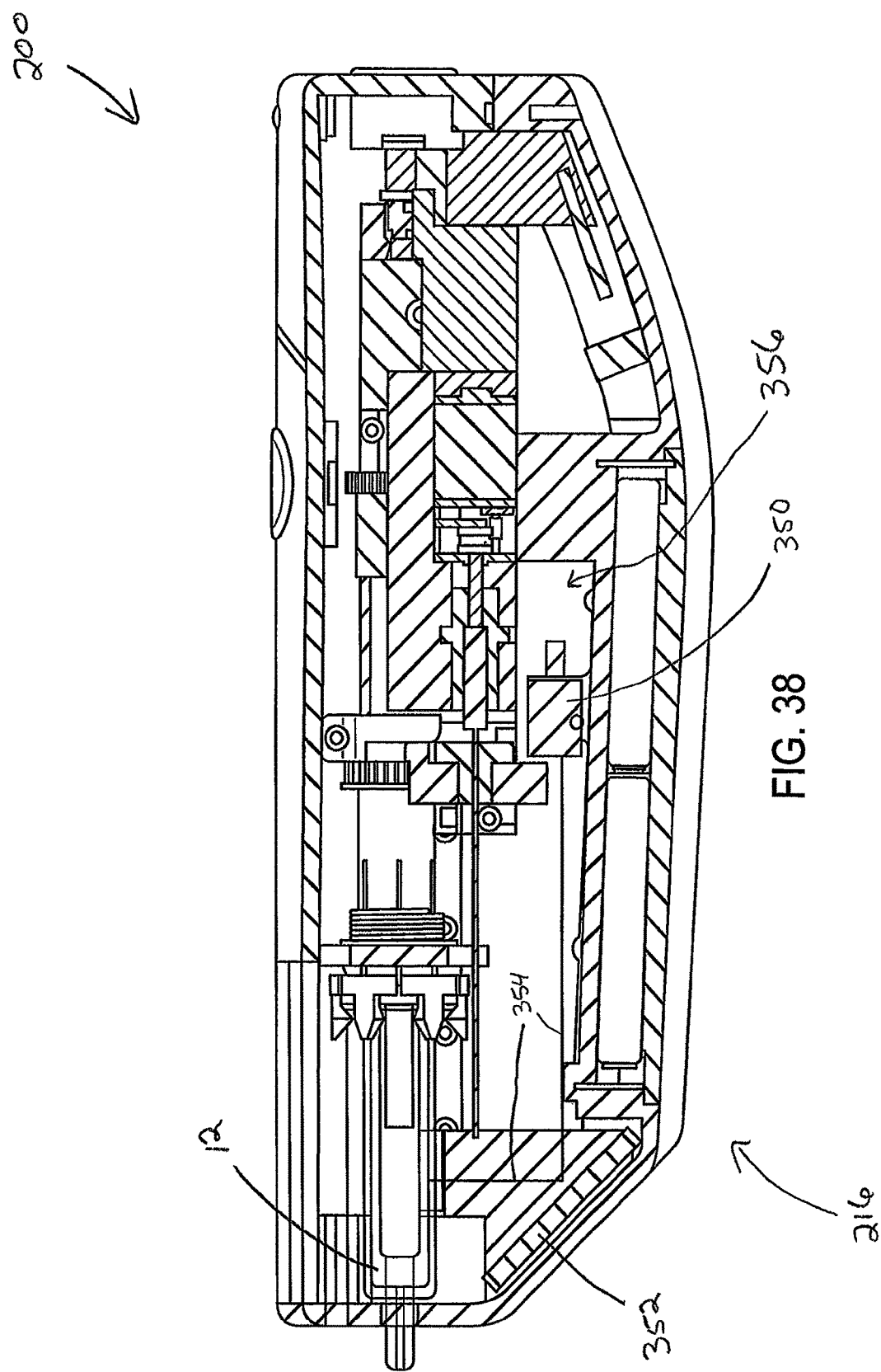
FIG. 38 is a cross-sectional view of a scan assembly of an injection device in accordance with an embodiment of the present invention.

Referring to FIG. 38, in one embodiment, the battery compartment 274 may be located at a bottom portion of the injection device 200. In other embodiments, the battery compartment 274 may be located at a back end, e.g., the second end 263, to allow a less obstructed line of sight for a barcode scanner 350 of the scan assembly 216 of the injection device 200.

Referring to FIGS. 27-30, the injection device 200 includes an engagement assembly 210 adapted to be removably engageable to each of the respective pre-filled containers 12. With the injection device 200 engaged with a respective pre-filled container 12, the injection device 200 is adapted to automatically actuate a plunger rod 264 to expel the medication from the respective pre-filled container 12.

Referring to FIGS. 27-30, in one embodiment, the engagement assembly 210 includes a connection element 300 comprising a body portion 302 defining a cavity 303 therethrough and a connection ring 304 including a plurality of syringe grip members 306 each having a locking hook protrusion 308 and an angled wall 310.

Referring to FIGS. 27-30, in one embodiment, the plurality of syringe grip members 306 each have a locking hook protrusion 308 and an angled wall 310. In one embodiment, syringe grip members 306 are elastically deformable. For example, the syringe grip members 306 can snap around a flange 140 of a container 12 to securely grip and/or engage a respective container 12. Syringe grip members 306 are attachable to a container 12 to secure a container 12 to the injection device 200 via the connection element 300. Each syringe grip member 306 includes a locking hook protrusion 308 arranged to engage a corresponding flange 140 (FIGS. 5A and 5B) on a container 12 as shown in FIGS. 28 and 30.

Connection element 300 of engagement assembly 210 of injection device 200 may be dimensioned to be attached to containers of any size and volume. In other embodiments, connection element 300 of engagement assembly 210 of injection device 200 may include other connection mechanisms for securing a container 12 to the injection device 200 such as a threaded portion, a snap fit mechanism, locking tabs, or other similar mechanism.

Referring to FIG. 27, each syringe grip member 306 includes an angled wall 310 arranged to provide a first lead-in surface 312 to center and align the connection element 300 on a container 12 during initial engagement of the container 12 to the injection device and a second lead-in surface 314 for ejection of a container 12 after injection is complete.

Figure 4:
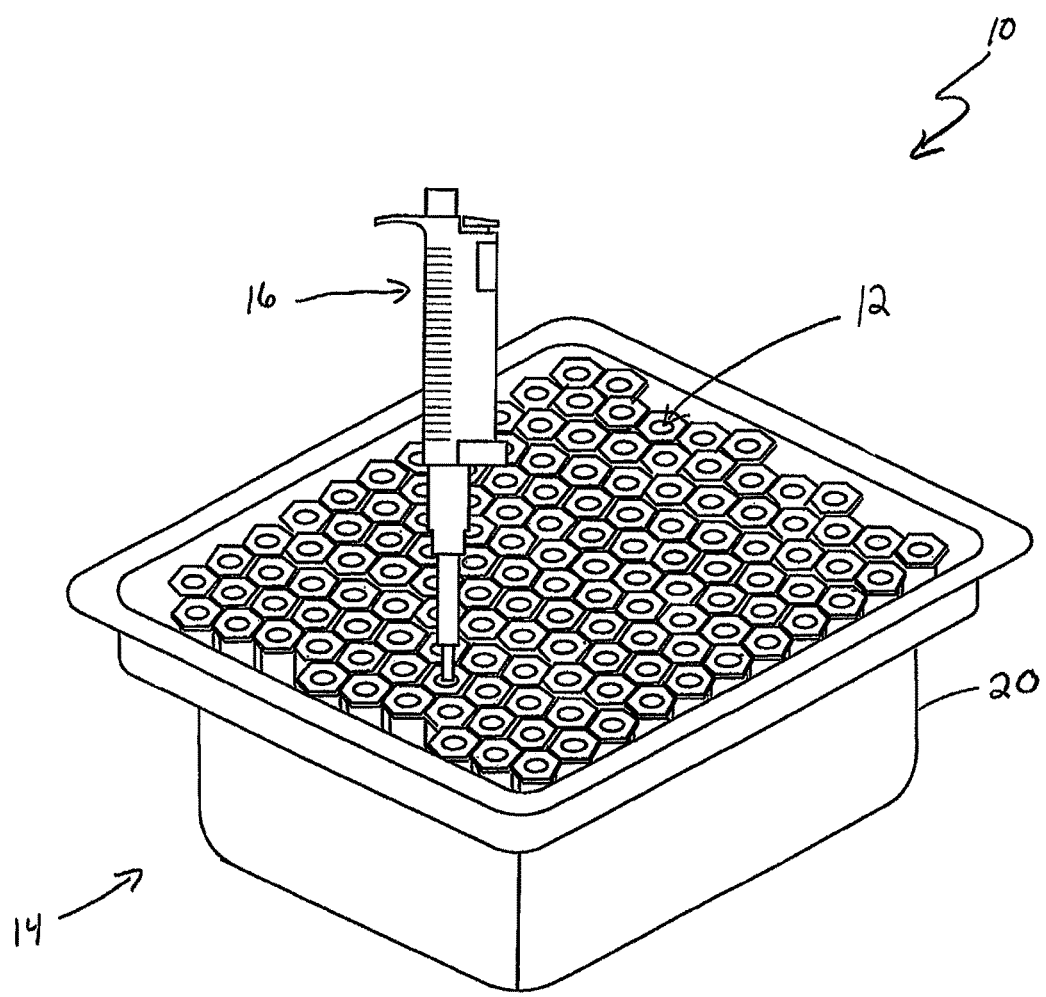
FIG. 4 is a perspective view of a packaging unit and an injection device of a drug storage and dispensing system for a plurality of pre-filled containers in accordance with an embodiment of the present invention.

Referring to FIGS. 29 and 30, in one embodiment, the number of syringe grip members 306 are designed to fit into the gaps 316 between respective containers 12 in a packaging unit 14 (FIG. 4). The number of syringe grip members 306 are also designed to grip containers with round and cut flanges. Connection element 300 of engagement assembly 210 of injection device 200 allows the injection device 200 to be secured to a container 12 while a container 12 is contained within the packaging unit 14 (FIG. 4). Additionally, the container 12 can be removed from the packaging unit 14 easily using the injection device 200.

Referring to FIGS. 31-34, the injection device 200 includes a retraction assembly 212. After a container 12 is removed from the packaging unit 14 using the injection device 200 via the securement engagement of the container 12 to the engagement assembly 210 of the injection device 200, the retraction assembly 212 is adapted to retract a pre-filled container 12 into the injection device 200.

Figure 20:
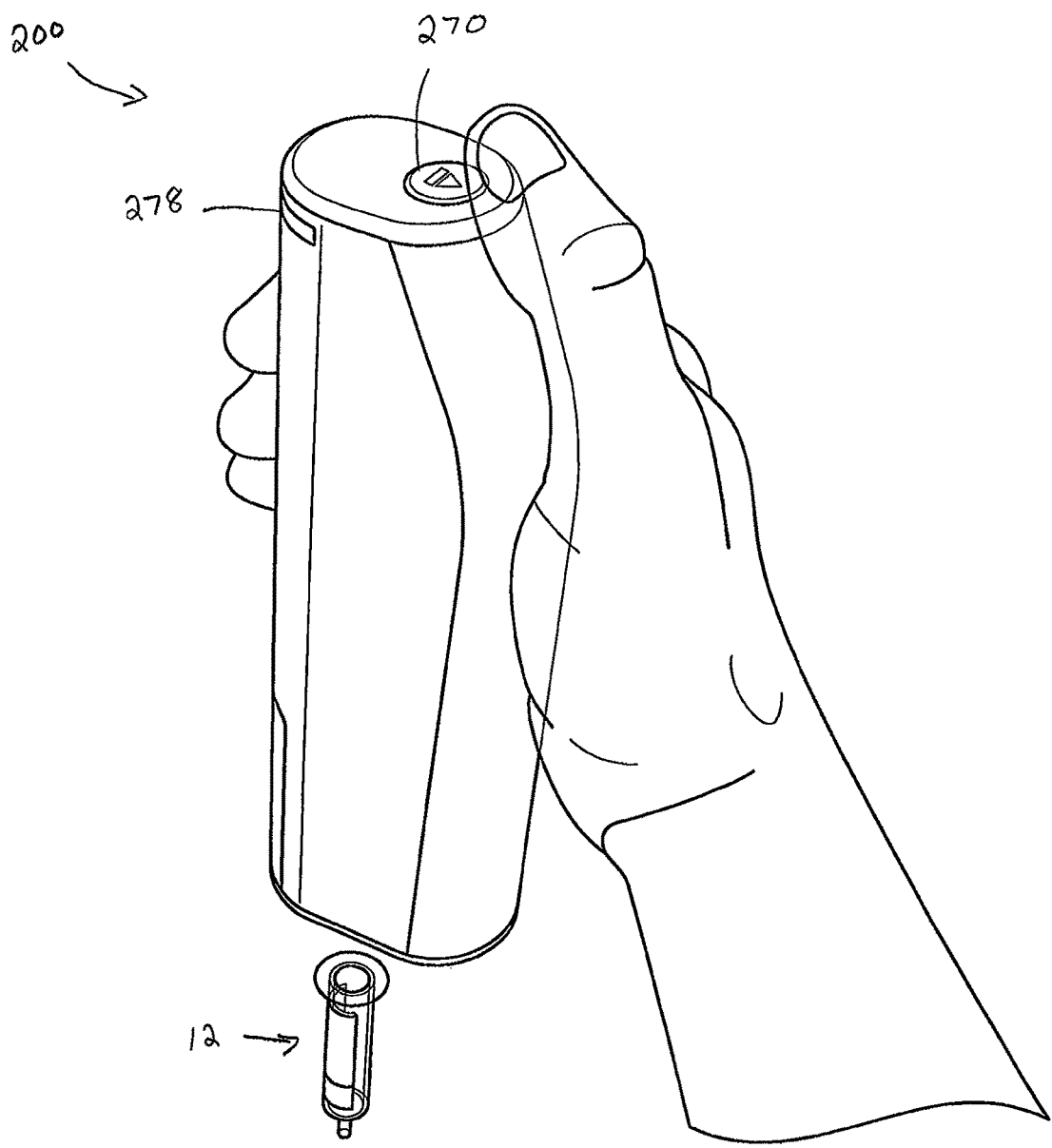
FIG. 20 is a perspective view of a second step of using an injection device of the present disclosure in accordance with an embodiment of the present invention.

In one embodiment, the retraction assembly 212 is transitionable between a first position (FIGS. 31 and 33) in which the plurality of syringe grip members 306 are outside the injection device 200 to engage a pre-filled container 12 and a second position (FIGS. 32 and 34) in which the pre-filled container 12 is contained within the injection device 200. In one embodiment, actuation of the retraction assembly 212 between the first and second positions is activated by a user pressing the top or first button 270 (FIG. 20).

Referring to FIGS. 31-34, in one embodiment, the retraction assembly 212 includes a rail 320, a carriage 322, connection elements 324, a carriage lead screw 326, an adapter 328, a motor 330, and limit switches 332.

In one embodiment, the rail 320 is positioned between a top housing portion 266 and a bottom housing portion 268. In one embodiment, the rail 320 is linear and provides guidance for the components of the retraction assembly 212 that are movable to retract a container 12 within the injection device 200.

The carriage 322 is movably attached to the rail 320. For example, in one embodiment, the carriage 322 is movably attached to the rail 320 via the connection elements 324 that are slidable on the rail 320. In one embodiment, motion for the carriage 322 along the rail 320 is provided by the carriage lead screw 326. In one embodiment, the adapter 328 is in communication with the carriage lead screw 326 and the motor 330. In this manner, the motor 330 is able to turn the carriage lead screw 326 that moves the carriage 322 between the first and second positions. In one embodiment, the limit switches 332 are provided to control how far the carriage 322 can travel within the injection device 200.

In one embodiment, a portion of the engagement assembly 210 is connected to a portion of the retraction assembly 212. In this manner, retraction of the carriage 322 from the first position (FIGS. 31 and 33) to the second position (FIGS. 32 and 34) retracts a container 12 secured to the engagement assembly 210 within the injection device 200.

Referring to FIGS. 35-37, the injection device 200 includes a locking assembly 214. After a container 12 is removed from the packaging unit 14 using the injection device 200 via the securement engagement of the container 12 to the engagement assembly 210 of the injection device 200 and the retraction assembly 212 is used to retract a pre-filled container 12 into the injection device 200, the locking assembly 214 is adapted to lock the plurality of syringe grip members 306 to the container 12.

The locking assembly 214 is adapted to lock the plurality of syringe grip members 306 to the container 12 with the retraction assembly 212 in the second position (FIGS. 32 and 34), e.g., with the container 12 within the injection device 200.

Referring to FIGS. 35-37, in one embodiment, the locking assembly 214 includes a locking ring 340, a boss 342, and a compression spring 344. Referring to FIG. 35, in one embodiment, the boss 342 located within the injection device 200 stops and/or abuts the locking ring 340. Referring to FIG. 35, with the retraction assembly 212 in the first position (FIGS. 31 and 33), e.g., in which the plurality of syringe grip members 306 are outside the injection device 200 to engage a pre-filled container 12, the locking ring 340 is stopped against the boss 342. In this manner, the syringe grip members 306 are outside the injection device 200 and are free to flex to engage a pre-filled container 12.

Referring to FIGS. 36 and 37, with the retraction assembly 212 being moved to the second position, the compression spring 344 moves the locking ring 340 over the syringe grip members 306 of the engagement assembly 210. In this manner, with the locking ring 340 engaged with the syringe grip members 306, the syringe grip members 306 are prevented from flexing outward thereby locking the plurality of syringe grip members 306 to a container 12. This keeps the container 12 from inadvertently getting pulled out of the injection device 200 by a user or pushed out of the injection device 200 due to the force applied to the plunger rod 264 during injection.

Referring to FIGS. 38-42, the injection device 200 includes a scan assembly 216 and a rotation assembly 218. Referring to FIGS. 38-42 and 49A-49B, in one embodiment, a container 12 includes a barcode 290 containing information and the injector device 200 includes a scan assembly 216 adapted to scan the barcode 290 with the container 12 in the second position. The injection device 220 also includes a rotation assembly 218 for rotating the container 12 with the container 12 in the second position. The rotation assembly 218 ensures that no matter an initial position of a container 12 securely received within an injection device 200, the rotation assembly 218 is adapted to rotate the container 12 until the scan assembly 216 is able to properly scan the barcode 290 of a container 12. Because the barcode 290 of a container 12 could be at any position around the perimeter of a container 12, the rotation assembly 218 is able to rotate the container 12 at least one (1) revolution during the barcode scanning process to ensure that the barcode 290 is able to be seen by the scan assembly 216.

Figure 41:
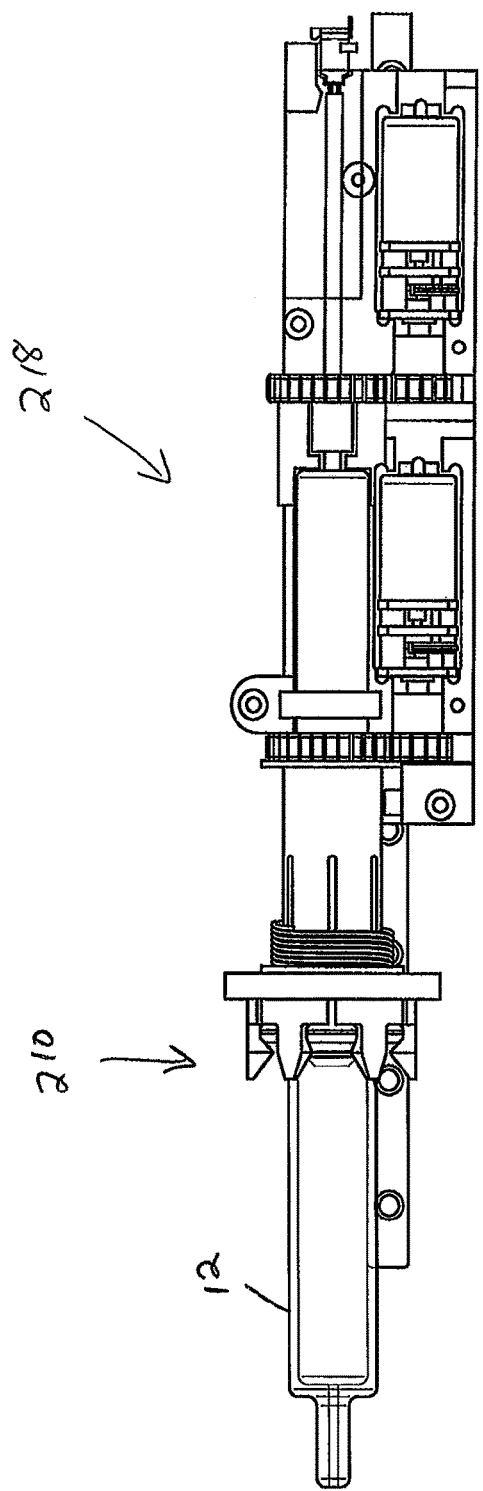
FIG. 41 is a side partial cross-sectional view of a rotation assembly of an injection device in accordance with an embodiment of the present invention.
Figure 42:
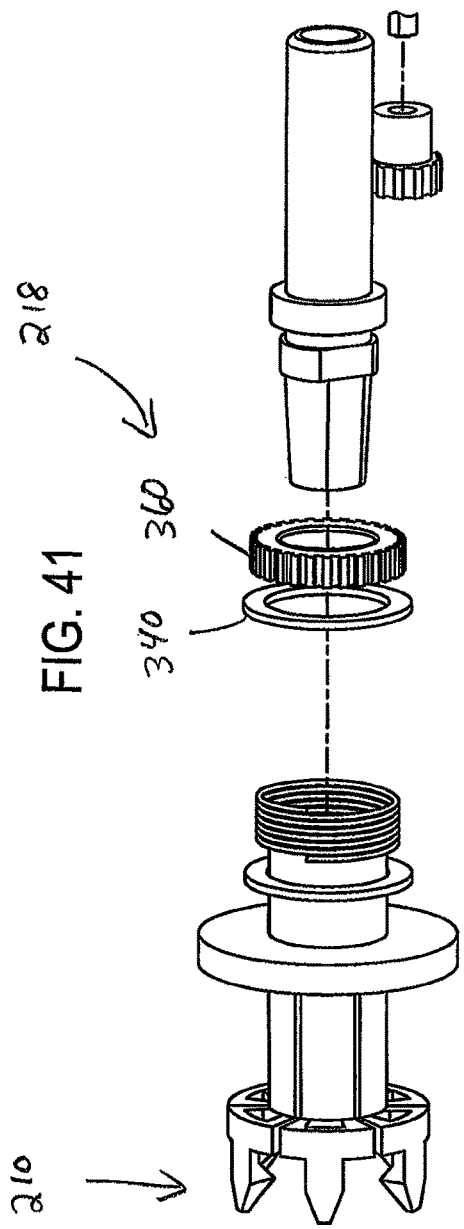
FIG. 42 is an exploded, perspective view of a rotation assembly of an injection device in accordance with an embodiment of the present invention.

Referring to FIGS. 39 and 40, in one embodiment, the rotation assembly 218 includes a rotational gear 360 in communication with a motor 362. The rotational gear 360 is also in communication with the engagement assembly 210. In this manner, when the motor 362 is actuated, the rotational gear 360 is rotated thereby rotating the engagement assembly 210 and the container 12. Referring to FIGS. 41 and 42, in one embodiment, the rotation assembly 218 is rotatable while the engagement assembly 210 is securely held so that the container 12 remains stable and does not rattle or vibrate.

After a container 12 is locked within the injection device 200, the scan assembly 216 is able to scan the barcode 290 of a container 12. In one embodiment, the scan assembly 216 includes a barcode scanner 350, a mirror 352, a scanner optical path 354, and a transmitter 356 for transmitting the information scanned from the barcode 290. In this manner, after the barcode scanner 350 of the scan assembly 216 scans the barcode 290 of a container 12, the transmitter 356 of the scan assembly 216 is able to transmit the information from the barcode 290 to a remote system or electronic database, such as a computer 500 (FIG. 48). The electronic database and/or computer 500 receives the information transmitted from the transmitter 356 of the scan assembly 216 of the injection device 200. Next, the electronic database and/or computer 500 is adapted to verify the information contained on the barcode 290 and transmit a signal to the injection device 200 that provides positive feedback for injection using the injection device 200. In one embodiment, the injection device 200 is not able to inject a medication contained within a container 12 until the positive feedback is received from the electronic database and/or computer 500. This provides an important safety feature of the present disclosure. The electronic database and/or computer 500 is able to determine if a medication is incorrect or expired, and in such a case, the electronic database and/or computer 500 would not send positive feedback to the injection device 200 thereby preventing an unwanted medication from being injected into a patient.

The scan assembly 216 of the injection device 200 allows the injection device 200 to be a smart device that can capture, store, and transmit information about its usage. In one embodiment, the injection device 200 is equipped with an on-board electronic module comprising a non-volatile memory that can record and store container unique identification information, as well as time stamping information relative to the usage of a pre-filled container 12. The injection device electronic module is also equipped with a global positioning system (GPS) receiver that can record and store latitude and longitude coordinates of usage location. When used indoor, the injection device electronic module is compatible with existing indoor positioning systems using triangulation from wireless signal receivers.

In one embodiment, the injection device electronic module is also equipped with a wireless communication module able to establish distant communication by way of one or several of the following methods: near field communication (NFC), Bluetooth low energy (BLE), Wi-Fi, ZigBee, and/or GSM. The injection device electronic module comprises an embedded piece of software which can encrypt the collected information prior to its transmission. The information collected by the injection device can therefore be securely transmitted to a distant recipient by any of the above means. Examples of recipients are: a smartphone, a tablet, and/or a data management platform. In order to visualize transmitted data, application software is developed for all of the above hardware platforms. In case the information is sent to a distant data management platform, the visualization can happen either on a smartphone, a tablet, or a web portal that can also be accessed from an internet-connected computer.

As discussed above, the container 12 may include a unique identifier, e.g., a barcode 290, that the injection device 200 can read the information contained therein and either store it in its on-board non-volatile memory, or transmit it to a nearby smartphone or to a distant data management system, e.g., computer 500. Similarly, prefilled containers may be equipped with sensors such as temperature/humidity or shock/abuse sensors. Signals from those sensors can be read by the injection device 200 upon pick-up. If an abnormal condition is detected, an indicator present on the injection device 200 will alert the user and an optional interlock can prevent from proceeding with the injection. Once the container is picked-up and no abnormal container condition is detected, the healthcare worker proceeds with the injection using the injection device 200.

Referring to FIGS. 43-46, the injection device 200 includes an actuator assembly 220. Once positive feedback regarding the contents of a container 12 is received by the injection device 200, the actuator assembly 220 automatically actuates the plunger rod 264 of the injection device 200 to expel a medication from a pre-filled container 12.

Referring to FIGS. 43-46, in one embodiment, the actuator assembly 220 includes a plunger rod 264, a plunger lead screw 370, a plunger lead screw nut 372, a plunger lead screw gear 374, and a motor 376. The plunger lead screw 370 is in communication with the plunger rod 264. Referring to FIG. 43, in one embodiment, the plunger lead screw 370 is secured to a portion of the plunger rod 264. For example, the plunger lead screw 370 may be glued to a portion of the plunger rod 264.

Figure 45:
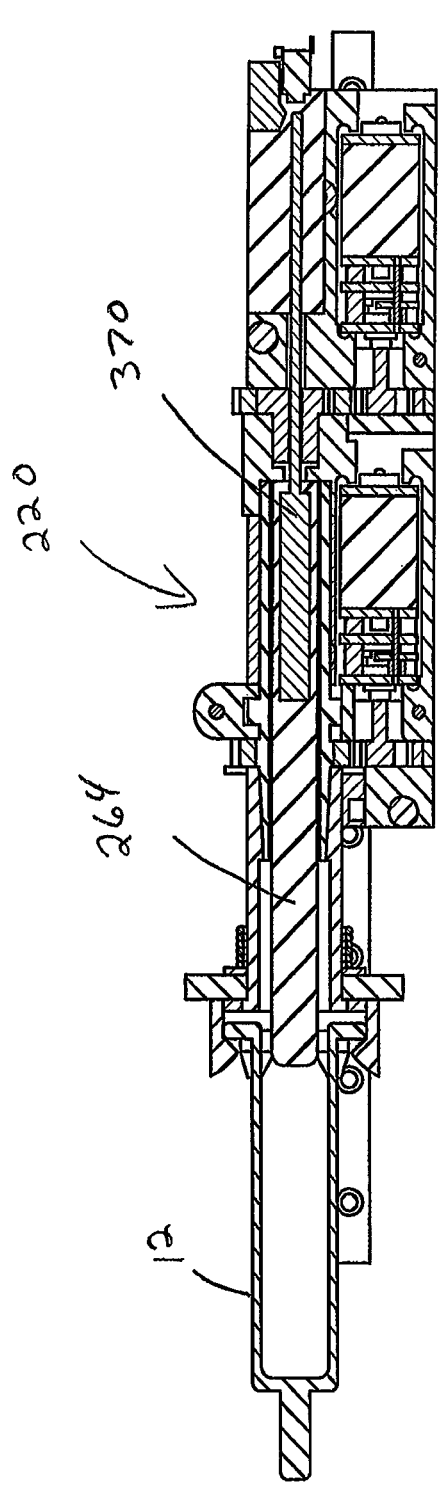
FIG. 45 is a cross-sectional view of an actuator assembly of an injection device in accordance with an embodiment of the present invention.
Figure 46:
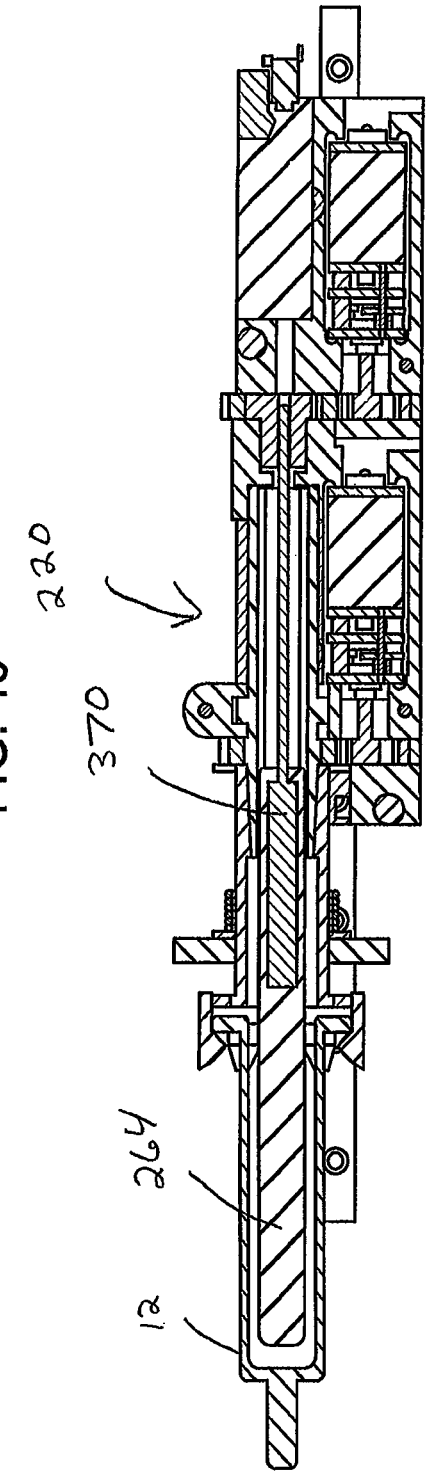
FIG. 46 is a cross-sectional view of an actuator assembly of an injection device in accordance with an embodiment of the present invention.

In one embodiment, the motor 376 drives the gear 374 which turns the nut 372. Referring to FIGS. 45 and 46, as the nut 372 turns, the nut 372 moves the plunger lead screw 370 linearly to actuate the plunger rod 264 to expel a medication from a container 12. Referring to FIGS. 45 and 46, the plunger rod 264 travels linearly through the center of the engagement assembly 210.

Referring to FIGS. 49A-B and 50A-B, a first pre-filled container 400 includes a first medication 402 and a first barcode 404 and a second pre-filled container 410 includes a second medication 412 and a second barcode 414. Although FIGS. 49A-B and 50A-B illustrate a general container, any container can be used in connection with an injection device of the present disclosure for an injection procedure. For example, a container and/or syringe as shown in FIGS. 1, 4, 5A, 5B, or similar container or syringe, can be used in connection with an injection device of the present disclosure.

The engagement assembly 210 of the injection device 200 is adapted to be removably engageable to the first pre-filled container 400 and the second pre-filled container 410.

With the injection device 200 engaged with the first pre-filled container 400, the injection device 200 is configured to automatically actuate the plunger rod 264 to expel the first medication 402 from the first pre-filled container 400.

With the injection device 200 engaged with the second pre-filled container 410, the injection device 200 is adapted to automatically actuate the plunger rod 264 to expel the second medication 412 from the second pre-filled container 410.

With the first container 400 contained within the injection device 200, the scan assembly 216 is adapted to scan the first barcode 404.

With the second container 410 contained within the injection device 200, the scan assembly 216 is adapted to scan the second barcode 414.

Figure 47:
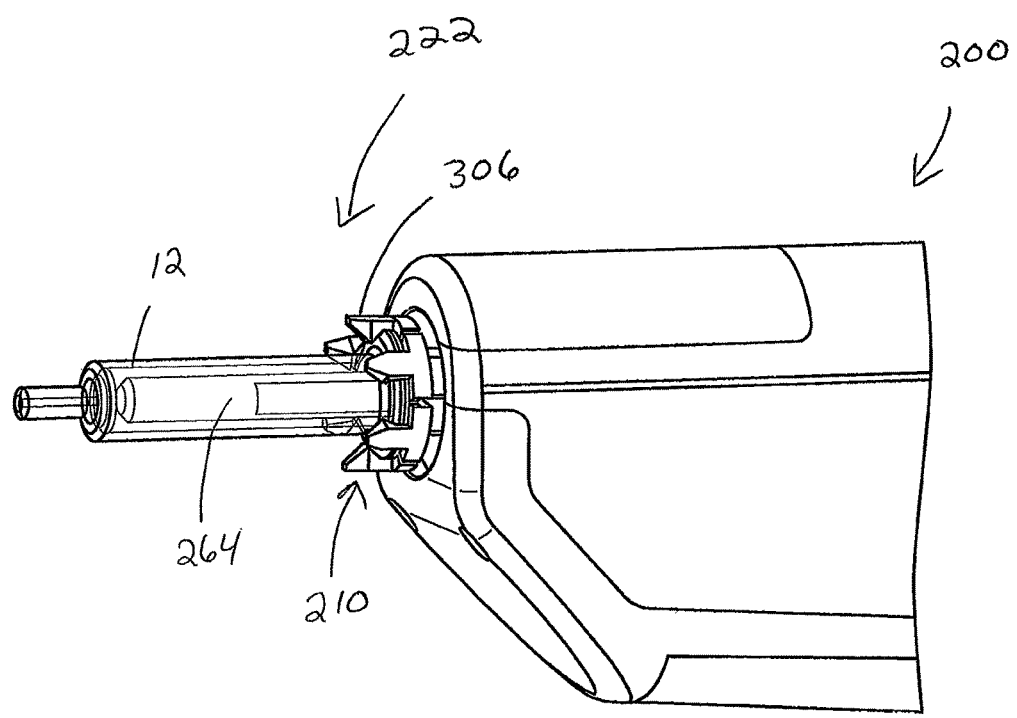
FIG. 47 is a partial perspective view of an ejection assembly of an injection device in accordance with an embodiment of the present invention.
Figures 49A, 49B:
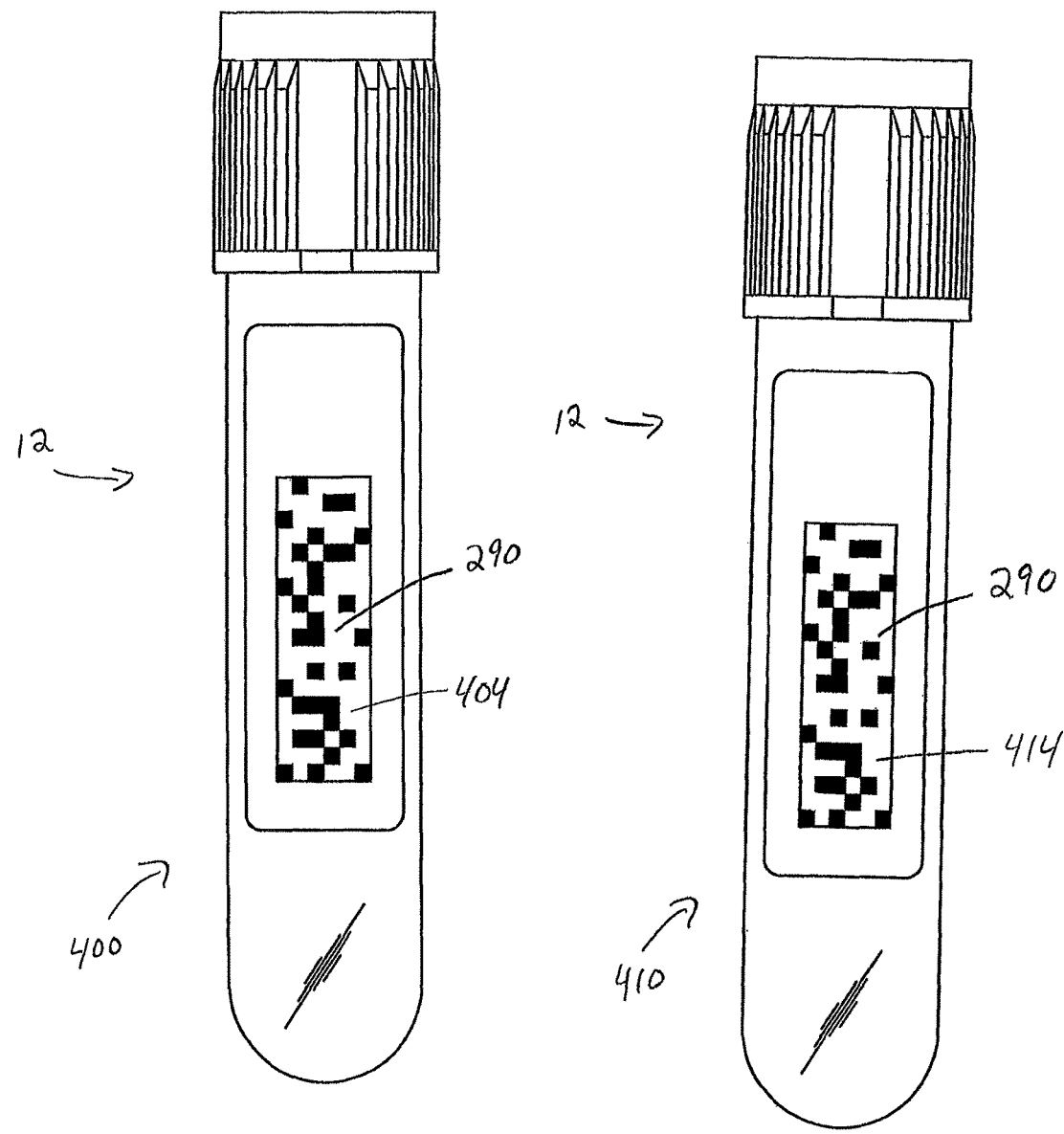
FIG. 49A is a side view of a first container for an injection device in accordance with an embodiment of the present invention.
FIG. 49B is a side view of a second container for an injection device in accordance with an embodiment of the present invention.
Figures 50A, 50B:
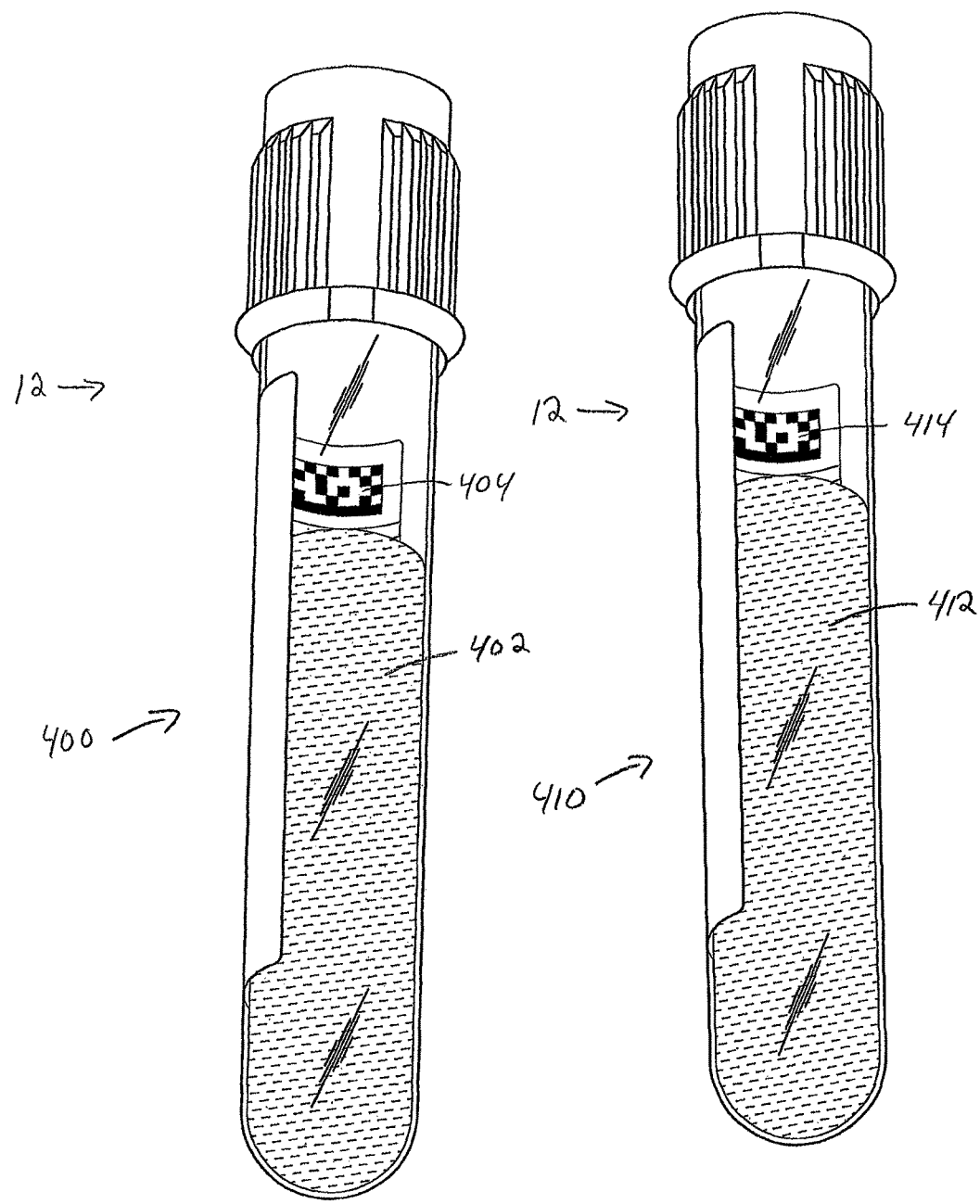
FIG. 50A is a perspective view of a first container for an injection device in accordance with an embodiment of the present invention.
FIG. 50B is a perspective view of a second container for an injection device in accordance with an embodiment of the present invention.

Referring to FIG. 47, the injection device 200 includes an ejection assembly 222 adapted to automatically eject a container 12 from the injection device 200. After an injection is complete, the injection device 200 has the ability to automatically eject a container 12 after it is moved back to the first position. In this manner, a user does not have to grab any portion of the container 12 to manually remove the container 12. In one embodiment, once a container 12 is positioned outside of the injector device 200 as shown in FIG. 47, the plunger rod 264 is extended a little farther pushing the container 12 out of engagement with the syringe grip members 306 thereby automatically ejecting the container 12 from the injection device 200.

Referring to FIGS. 19-24, a use of the injection device 200 will now be described.

Figure 19:
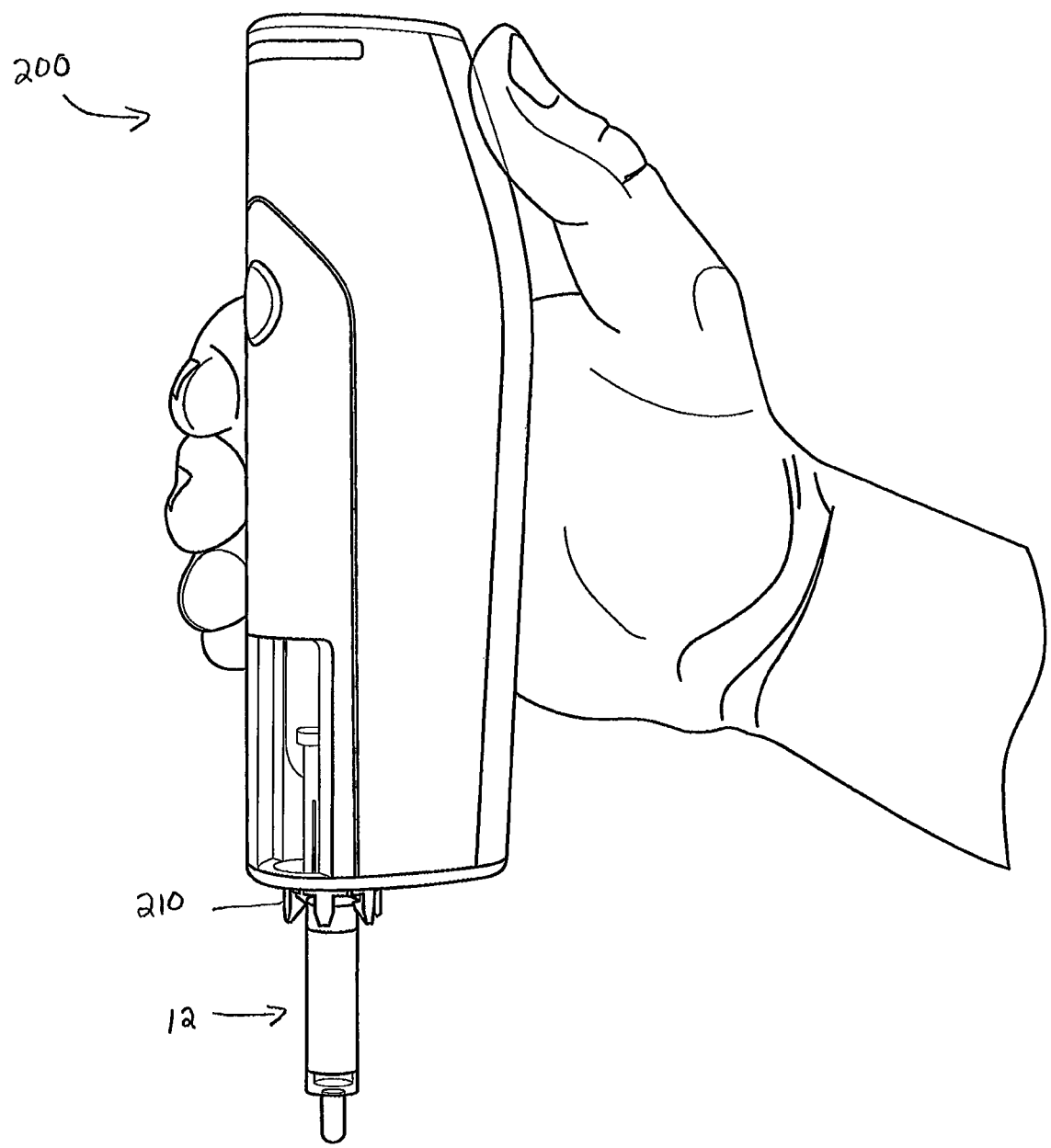
FIG. 19 is a perspective view of a first step of using an injection device of the present disclosure in accordance with an embodiment of the present invention

Referring to FIGS. 4 and 19, a user or a healthcare worker ready to administer a treatment may first select a pre-filled drug container 12 contained within the packaging unit 14 for injection using the injection device 200. A downward vertical motion is used for container loading to the injection device 200. As described above, the engagement assembly 210 is used to securely engage a container 12 to the injection device 200. Once the container 12 is securely engaged with the injection device 200, the injection device 200 is used to pick-up and remove the container 12 from the packaging unit 14.

In one embodiment, as described above, during removal of the pre-filled container 12 from the container holding portion 48 of the packaging unit 14, the deformable fins 52 of the nest member 22 of the packaging unit 14 allow for automatic removal of a needle shield 102 of a respective pre-filled container 12. In this manner, the packaging unit 14 allows for the needle shield 102 to be automatically removed and may remain inside the nest member 22 when picking up the pre-filled container 12, e.g., syringe 100.

Next, referring to FIG. 20, a user may press the first or top button 270 to activate the retraction assembly 212 (FIGS. 31-34) to automatically retract a container 12 into the injection device 200 as described above. Subsequently, with the retraction assembly 212 in the second position (FIGS. 32 and 34) with the pre-filled container 12 within the injection device 200, the locking assembly 214 (FIGS. 35-37) locks the plurality of syringe grip members 306 to the pre-filled container 12.

Next, the scan assembly 216 (FIGS. 38-42) and rotation assembly 218 (FIGS. 38-42) automatically scan a barcode of the container 12 as described above. In this manner, after the barcode scanner 350 of the scan assembly 216 scans the barcode 290 of a container 12, the transmitter 356 of the scan assembly 216 is able to transmit the information from the barcode 290 to a remote system or electronic database, such as a computer 500 (FIG. 48). The electronic database and/or computer 500 receives the information transmitted from the transmitter 356 of the scan assembly 216 of the injection device 200. Next, the electronic database and/or computer 500 is adapted to verify the information contained on the barcode 290 and transmit a signal to the injection device 200 that provides positive feedback for injection using the injection device 200. In one embodiment, the injection device 200 is not able to inject a medication contained within a container 12 until the positive feedback is received from the electronic database and/or computer 500. This provides an important safety feature of the present disclosure. For example, referring to FIG. 21, in one embodiment, after positive feedback is received by the injection device 200, the indicator portion 278, such as an indicator light, is activated to notify the user of a correct barcode scan and injector status. The electronic database and/or computer 500 is able to determine if a medication is incorrect or expired, and in such a case, the electronic database and/or computer 500 would not send positive feedback to the injection device 200 thereby preventing an unwanted medication from being injected into a patient.

The scan assembly 216 of the injection device 200 allows the injection device 200 to be a smart device that can capture, store, and transmit information about its usage. In one embodiment, the injection device 200 is equipped with an on-board electronic module comprising a non-volatile memory that can record and store container unique identification information, as well as time stamping information relative to the usage of a pre-filled container 12. The injection device electronic module is also equipped with a global positioning system (GPS) receiver that can record and store latitude and longitude coordinates of usage location. When used indoor, the injection device electronic module is compatible with existing indoor positioning systems using triangulation from wireless signal receivers.

Figure 21:
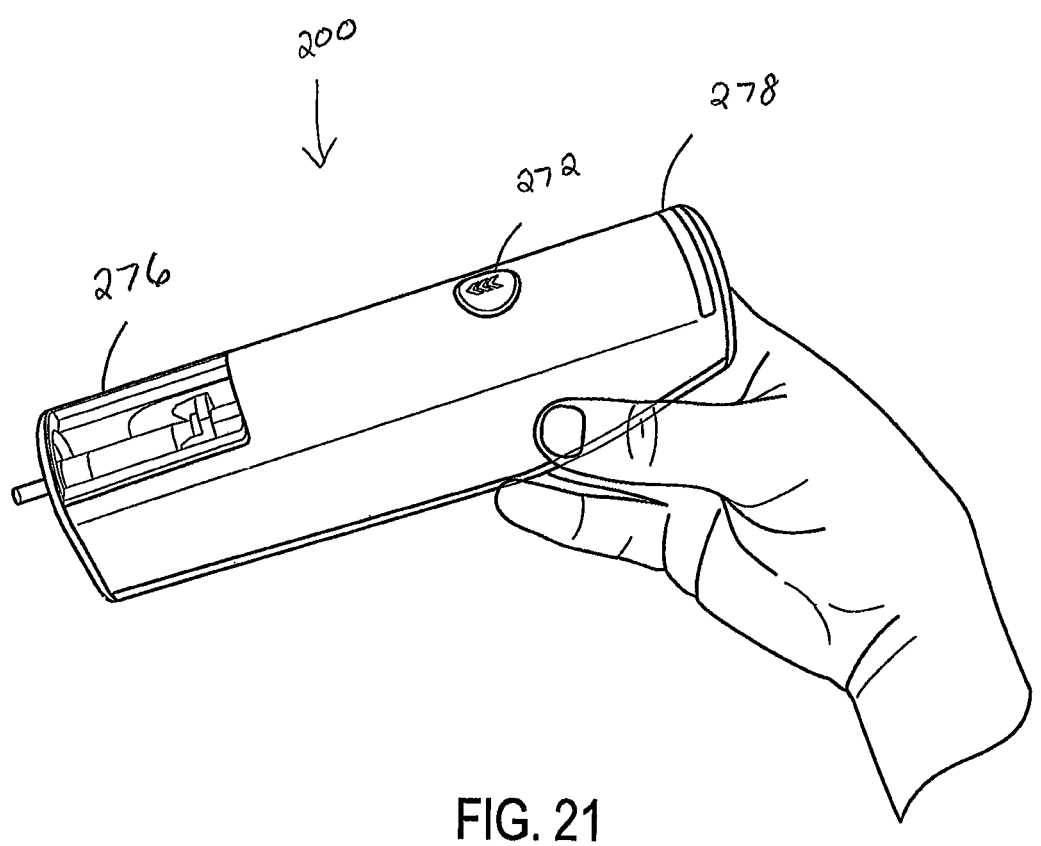
FIG. 21 is a perspective view of a third step of using an injection device of the present disclosure in accordance with an embodiment of the present invention.

Referring to FIG. 21, after positive feedback is received by the injection device 200, the transparent window 276 allows a user to present to a patient the injection device 200 with container 12 for viewing before injection.

Figure 22:
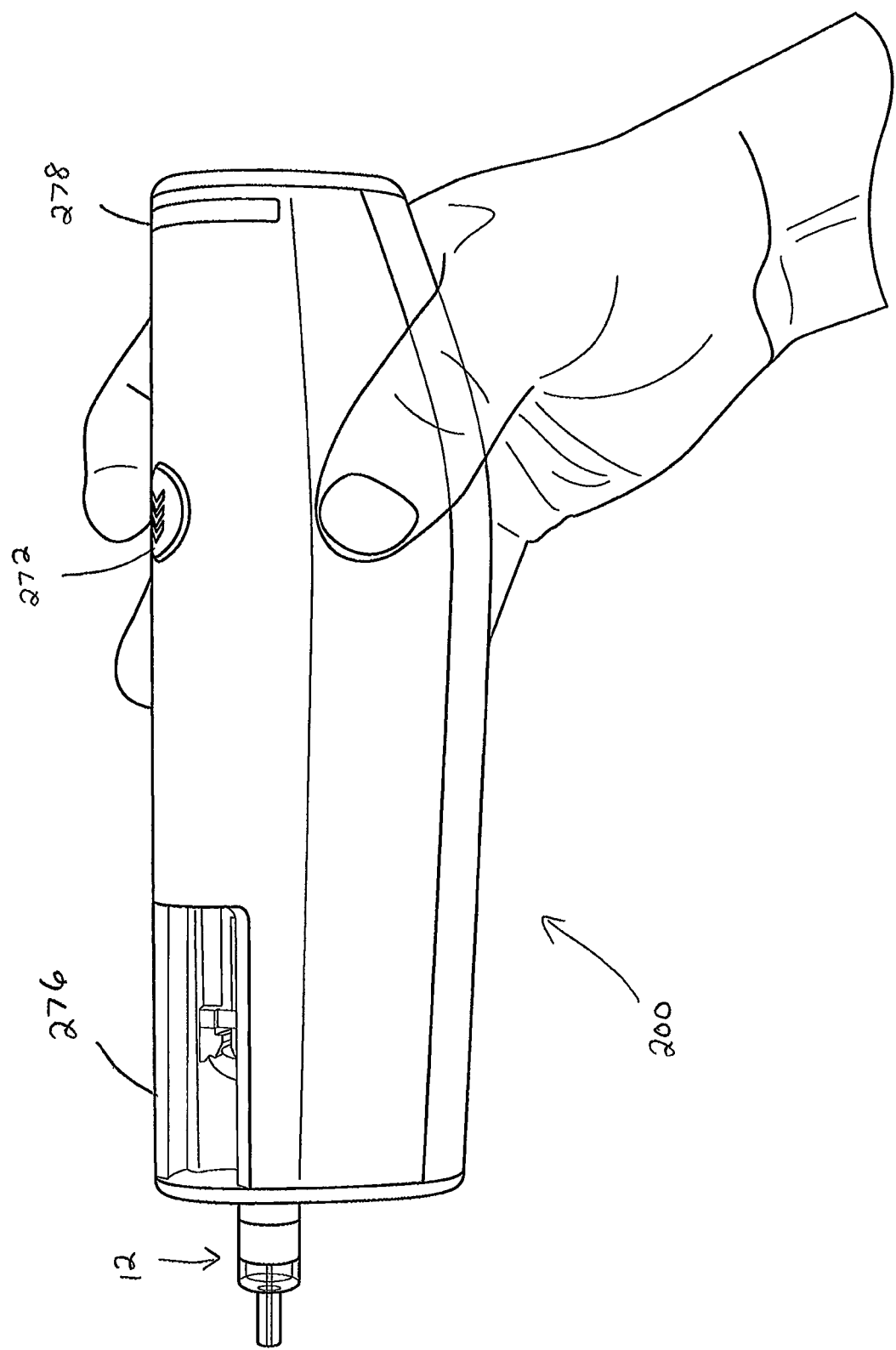
FIG. 22 is a perspective view of a fourth step of using an injection device of the present disclosure in accordance with an embodiment of the present invention.

Next, referring to FIG. 22, in one embodiment, after successful reading of the barcode 290 of a container 12, the container may be translated into a needle attachment/injection position. The user may then remove a safety cap and attach a needle to a container, such as a syringe. In this manner, having a container, such as a syringe, extended from the injection device 200 during injection reduces a risk of splash back contamination.

Figure 23:
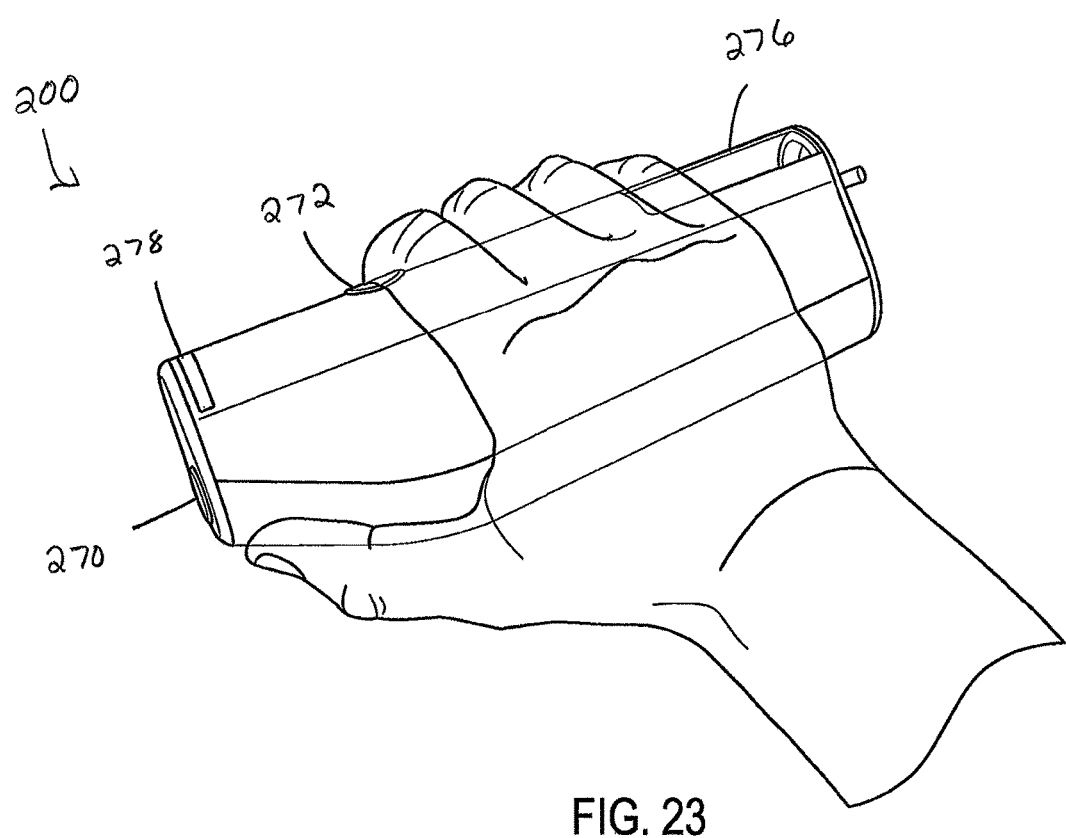
FIG. 23 is a perspective view of a first step of using an injection device of the present disclosure in accordance with an embodiment of the present invention

Referring to FIG. 23, the configuration of a user's hand to the injection device 200 during injection is shown. In this position, the injection device 200 can be securely held and the side or second button 272 pushed to activate the actuator assembly 220 (FIGS. 43-46) for injection of a medication or vaccine.

Figure 24:
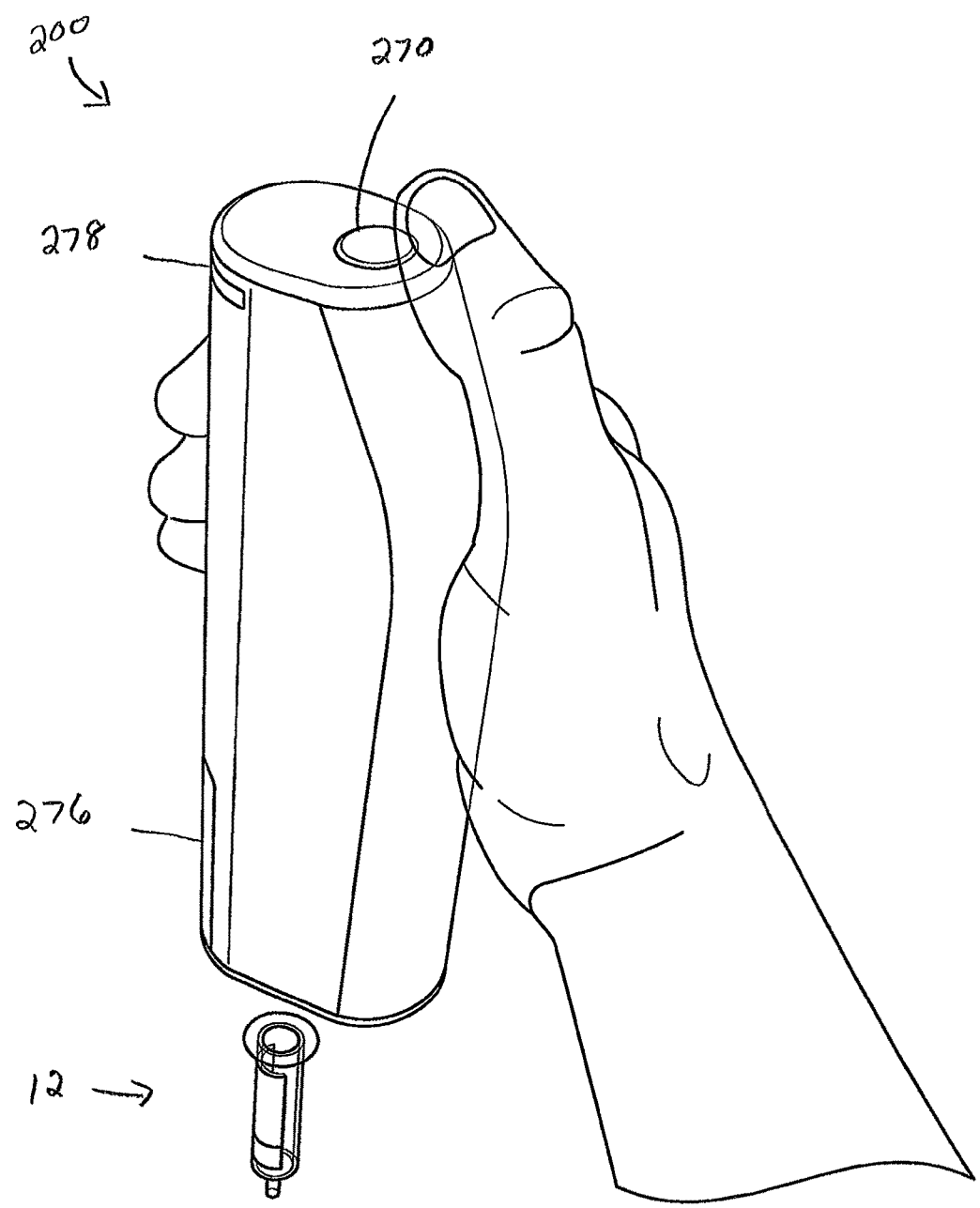
FIG. 24 is a perspective view of a second step of using an injection device of the present disclosure in accordance with an embodiment of the present invention.

Referring to FIG. 24, after injection is complete, the top or first button 270 may be pushed to activate the ejection assembly 222 (FIG. 47) to eject a container from the injection device 200.

In one embodiment, the injection device 200 could incorporate a motorized-darting mechanism that inserts the selected syringe into the skin surface of a patient at the right pre-set depth. The pre-set depth of insertion is derived from reading the syringe identifier that bears information on the type of injection associated with the syringe.

In one embodiment, as discussed above, the syringe or container may include a unique identifier that the injection device 200 can read the information contained therein and either store it in its on-board non-volatile memory, or transmit it to a nearby smartphone or to a distant data management system. Similarly, prefilled containers may be equipped with sensors such as temperature/humidity or shock/abuse sensors. Signals from those sensors can be read by the injection device 200 upon pick-up. If an abnormal condition is detected, an indicator present on the injection device 200 will alert the user and an optional interlock can prevent from proceeding with the injection. Once the syringe is picked-up and no abnormal container condition is detected, the healthcare worker proceeds with the injection using the injection device 200.

The injection completion can optionally be sensed by the injection device 200, and the corresponding event can either be stored in its on-board non-volatile memory or transmitted to a nearby smartphone or to a distant data management system.

The drug storage and dispensing system 10 of the present disclosure can be used either in a traditional healthcare setting or outside of a traditional healthcare setting to deliver drugs on demand in a safe and quick manner. The drug storage and dispensing system 10 can also be used by patients suffering from chronic diseases who self-administer their injectable medication.

The drug storage and dispensing system 10 of the present disclosure is especially useful when used to perform vaccinations. Vaccination campaigns can be performed in a traditional healthcare setting, e.g., a doctor's office, hospitals, clinics, minute clinics, pharmacies, vaccination center, or similar settings, or in non-traditional settings, e.g., retail outlets such as supermarkets, schools, or offices, or in no particular setting and directly in contact with the targeted population as it is often the case in developing countries.

As described above, the injection device 200 allows for automatic injection of a medication from a selected pre-filled container 12. With the injection device 200 engaged with a respective pre-filled container 12, the injection device 200 is adapted to automatically actuate a plunger rod 264 to expel the medication from the respective pre-filled container 12.

In one embodiment, the injection completion can optionally be sensed by the injection device 200, and the corresponding event can either be stored in its on-board non-volatile memory or transmitted to a nearby smartphone or to a distant data management system.

Once injection is completed, a safety mechanism is triggered so that a sharp tip 129 of a cannula 128 cannot be accessed, thus preventing needle-associated injuries. For example, referring to FIGS. 8-10, the safety shield 108 is adapted to automatically shield a needle tip, e.g., sharp tip 129 of cannula 128, of a respective pre-filled container 12 after an injection is completed.

The drug storage and dispensing system 10 of the present disclosure can be used either in a traditional healthcare setting or outside of a traditional healthcare setting to deliver drugs on demand in a safe and quick manner. The drug storage and dispensing system 10 can also be used by patients suffering from chronic diseases who self-administer their injectable medication.

The drug storage and dispensing system 10 of the present disclosure is especially useful when used to perform vaccinations. Vaccination campaigns can be performed in a traditional healthcare setting, e.g., a doctor's office, hospitals, clinics, minute clinics, pharmacies, vaccination center, or similar settings, or in non-traditional settings, e.g., retail outlets such as supermarkets, schools, or offices, or in no particular setting and directly in contact with the targeted population as it is often the case in developing countries.

Pandemic situations require a medical practitioner to be able to vaccinate a large number of people in a very short amount of time. In all non-traditional vaccination settings, the drug storage and dispensing system 10 of the present disclosure is especially useful for the following reasons: (1) the drug storage and dispensing system 10 provides a faster and safe way of vaccinating more people per unit of time; (2) the drug storage and dispensing system 10 provides a means to optimize cold chain space by offering a denser packaging compared to other packaging systems for pre-filled containers; and (3) the drug storage and dispensing system 10 provides an automated capture and real-time transmission of vaccination data, thus enabling the precise tracking of vaccination coverage at a population level or accurate information in an individual vaccination log or electronic medical record at an individual level.

The drug storage and dispensing system 10 is envisioned to be a part of a novel service of an on-demand, mobile vaccination system. People wishing to be vaccinated can place their order online after responding to a short questionnaire on their current health status. Dispatching units that may be housed in nearby pharmacies would then prepare and group orders coming from their area of responsibility. Orders could then be loaded on a van or truck driven by a healthcare worker who goes on a vaccine delivery. A delivery itinerary and schedule could be optimized by a specific software and updated on-the-fly to account for any last minute change requests by a customer.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A packaging unit for a plurality of pre-filled containers each having a needle shield, the packaging unit comprising:
   a tub member defining a receiving cavity sized to receive the plurality of pre-filled containers therein; and
   a nest member securable within the tub member and having a plurality of container holding portions configured to receive respective pre-filled containers therein, each of the container holding portions having an engagement member comprising a plurality of elastically deformable fins adapted to engage within openings in the needle shield to automatically remove the needle shield of a respective pre-filled container upon removal of the respective pre-filled container from the container holding portion of the packaging unit.

2. The packaging unit of claim 1, further comprising a sealing member removably securable to the tub member.

3. The packaging unit of claim 2, wherein the sealing member is a cover.

4. The packaging unit of claim 1, wherein each of the pre-filled containers comprises a medication disposed therein.

5. A drug storage and dispensing system for a plurality of pre-filled containers each having a needle shield and containing a medication, the drug storage and dispensing system comprising:
   a packaging unit, comprising:
      a tub member defining a receiving cavity sized to receive the plurality of pre-filled containers therein; and
      a nest member securable within the tub member and having a plurality of container holding portions configured to receive respective pre-filled containers therein, each of the container holding portions having an engagement member adapted to automatically remove the needle shield of a respective pre-filled container upon removal of the respective pre-filled container from the container holding portion of the packaging unit; and
   an injection device for automatic injection of the medication from respective pre-filled containers, the injection device having an engagement portion adapted to be removably engageable to each of the respective pre-filled containers, the injection device having a plunger rod movably disposed within the injection device,
      wherein, with the injection device engaged with a respective pre-filled container, the injection device is configured to automatically actuate the plunger rod to expel the medication from the respective pre-filled container.

6. The drug storage and dispensing system of claim 5, wherein each of the pre-filled containers includes a readable information portion.

7. The drug storage and dispensing system of claim 6, wherein at least a part of the readable information portion is a barcode.

8. The drug storage and dispensing system of claim 6, wherein the injection device includes a scanner portion adapted to read the readable information portion of respective pre-filled containers.

9. The drug storage and dispensing system of claim 5, wherein each of the pre-filled containers includes a safety shield adapted to automatically shield a needle tip of a respective pre-filled container after an injection is completed.

10. The drug storage and dispensing system of claim 5, wherein the engagement portion of the injection device comprises a threaded portion.

11. A drug storage and dispensing system for a first pre-filled container having a first needle shield and containing a first medication and a second pre-filled container having a second needle shield and containing a second medication, the drug storage and dispensing system comprising:
 a packaging unit, comprising:
  a tub member defining a receiving cavity sized to receive the first pre-filled container and the second pre-filled container therein; and
  a nest member securable within the tub member and having a first container holding portion configured to receive the first pre-filled container therein and a second container holding portion adapted to receive the second pre-filled container therein, the first container holding portion having a first engagement member adapted to automatically remove the first needle shield of the first pre-filled container upon removal of the first pre-filled container from the first container holding portion of the packaging unit, the second container holding portion having a second engagement member adapted to automatically remove the second needle shield of the second pre-filled container upon removal of the second pre-filled container from the second container holding portion of the packaging unit; and
 an injection device for automatic injection of the first medication from the first pre-filled container and the second medication from the second pre-filled container, the injection device having an engagement portion adapted to be removably engageable to the first pre-filled container and the second pre-filled container, the injection device having a plunger rod movably disposed within the injection device,
 wherein, with the injection device engaged with the first pre-filled container, the injection device is configured to automatically actuate the plunger rod to expel the first medication from the first pre-filled container, and
 wherein, with the injection device engaged with the second pre-filled container, the injection device is adapted to automatically actuate the plunger rod to expel the second medication from the second pre-filled container.

12. The drug storage and dispensing system of claim 11, wherein the first pre-filled container and the second pre-filled container each include a readable information portion.

13. The drug storage and dispensing system of claim 12, wherein at least a part of the readable information portion is a barcode.

14. The drug storage and dispensing system of claim 12, wherein the injection device includes a scanner portion adapted to read the readable information portion of the first pre-filled container and the second pre-filled container.

15. The drug storage and dispensing system of claim 11, wherein the first pre-filled container and the second pre-filled container each include a safety shield adapted to automatically shield a respective needle tip of the first pre-filled container and the second pre-filled container after an injection is completed.

16. The drug storage and dispensing system of claim 11, wherein the engagement portion of the injection device comprises a threaded portion.

17. The drug storage and dispensing system of claim 11, wherein at least a part of the readable information portion is a radiofrequency identification tag.

18. An injection device for a first pre-filled container having a first medication and a second pre-filled container having a second medication, the injection device comprising an engagement assembly adapted to be removably engageable to the first pre-filled container and the second pre-filled container, the injection device having a plunger rod movably disposed within the injection device,
 wherein, with the injection device engaged with the first pre-filled container, the injection device is configured to automatically actuate the plunger rod to expel the first medication from the first pre-filled container, and
 wherein, with the injection device engaged with the second pre-filled container, the injection device is adapted to automatically actuate the plunger rod to expel the second medication from the second pre-filled container.

19. The injection device of claim 18, wherein the engagement assembly comprises a plurality of syringe grip members.

20. The injection device of claim 19, wherein the plurality of syringe grip members are elastically deformable.

21. The injection device of claim 19, further comprising a retraction assembly adapted to retract a pre-filled container into the injection device.

22. The injection device of claim 21, wherein the retraction assembly comprises a rail and a carriage movably attached to the rail.

23. The injection device of claim 21, wherein the retraction assembly is transitionable between a first position in which the plurality of syringe grip members are outside the injection device to engage the pre-filled container and a second position in which the pre-filled container is contained within the injection device.

24. The injection device of claim 23, wherein, with the retraction assembly in the second position with the pre-filled container within the injection device, the injection device further comprises a locking assembly adapted to lock the plurality of syringe grip members to the pre-filled container.

25. The injection device of claim 23, wherein the pre-filled container includes a readable information portion and the injector device further comprises a scan assembly adapted to scan the readable information portion with the pre-filled container in the second position.

26. The injection device of claim 25, further comprising a rotation assembly for rotating the pre-filled container with the pre-filled container in the second position.

27. The injection device of claim 25, wherein the readable information portion is at least one of a barcode, QR code, datamatrix and an RFID tag.

28. The injection device of claim 18, further comprising an actuator assembly,
   wherein, with the injection device engaged with the first pre-filled container, the actuator assembly automatically actuates the plunger rod to expel the first medication from the first pre-filled container, and
   wherein, with the injection device engaged with the second pre-filled container, the actuator assembly automatically actuates the plunger rod to expel the second medication from the second pre-filled container.

29. The injection device of claim 18, further comprising an ejection assembly adapted to automatically eject a pre-filled container from the injection device.

* * * * *